US007951785B2

(12) United States Patent
Anderson et al.

(10) Patent No.: US 7,951,785 B2
(45) Date of Patent: May 31, 2011

(54) NFIA IN GLIAL FATE DETERMINATION, GLIOMA THERAPY AND ASTROCYTOMA TREATMENT

(75) Inventors: David J Anderson, Altadena, CA (US); Ben Deneen, Alhambra, CA (US); Hae-Ri Song, Pasadena, CA (US)

(73) Assignees: California Institute of Technology, Pasadena, CA (US); Children's Hospital, Los Angeles, Los Angeles, CA (US)

(*) Notice: Subject to any disclaimer, the term of this patent is extended or adjusted under 35 U.S.C. 154(b) by 57 days.

(21) Appl. No.: 12/234,366

(22) Filed: Sep. 19, 2008

(65) Prior Publication Data

US 2009/0087434 A1 Apr. 2, 2009

Related U.S. Application Data

(60) Provisional application No. 60/994,753, filed on Sep. 21, 2007.

(51) Int. Cl.

*A61K 31/70* (2006.01)
*A61K 39/395* (2006.01)
*C07H 21/02* (2006.01)
*C07H 21/04* (2006.01)
*C12Q 1/68* (2006.01)

(52) U.S. Cl. ...... 514/44 A; 435/375; 435/377; 536/23.1; 536/24.1; 536/24.5; 424/130.1

(58) Field of Classification Search ........................ None
See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,816,567 | A | 3/1989 | Cabilly et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,868,116 | A | 9/1989 | Morgan et al. |
| 4,876,335 | A | 10/1989 | Yamane et al. |
| 4,904,582 | A | 2/1990 | Tullis |
| 4,948,882 | A | 8/1990 | Ruth et al. |
| 4,958,013 | A | 9/1990 | Letsinger |
| 4,980,286 | A | 12/1990 | Morgan et al. |
| 4,981,957 | A | 1/1991 | Lebleu et al. |
| 5,013,830 | A | 5/1991 | Ohtsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,166,320 | A | 11/1992 | Wu et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,223,409 | A | 6/1993 | Ladner et al. |
| 5,225,539 | A | 7/1993 | Winter |
| 5,235,033 | A | 8/1993 | Summerton et al. |
| 5,245,022 | A | 9/1993 | Weis et al. |
| 5,254,469 | A | 10/1993 | Warren et al. |
| 5,256,775 | A | 10/1993 | Froehler |
| 5,258,506 | A | 11/1993 | Urdea et al. |
| 5,262,536 | A | 11/1993 | Hobbs et al. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |

(Continued)

FOREIGN PATENT DOCUMENTS

EP 0 171 496 2/1986

(Continued)

OTHER PUBLICATIONS

Song et al., Neuro-Oncology vol. 12(2):122-132, 2010.* Acsadi G et al. "Human dystrophin expression in mdx mice after intramuscular injection of DNA constructs." Nature 352:815-18 (1991).

Altschul S F et al. "Basic Local Alignment Search Tool." J. Mol. Biol. 215:403-10 (1990).

Armentano D et al. "Expression of human factor IX in rabbit hepatocytes by retrovirus-mediated gene transfer: Potential for gene therapy of hemophilia B." Proc. Natl. Acad. Sci. USA 87:6141-45 (1990).

Current Protocols in Molecular Biology, Ausubel F M et al. (eds.) Greene Publishing Associates, Sections 9.10-9.14, 2009.

Barbas C F et al. "Assembly of combinatorial antibody libraries on phage surfaces: The gene III site." Proc. Natl. Acad. Sci. USA 88:7978-82 (1991).

Beerli R R et al. "Autocrine Inhibition of the Epidermal Growth Factor Receptor by Intracellular Expression of a Single-Chain Antibody." Biochem. Biophys. Res. Commun. 204(2):666-72 (1994).

(Continued)

*Primary Examiner* — Sean R McGarry

(74) *Attorney, Agent, or Firm* — Knobbe, Martens, Olson & Bear LLP

(57) ABSTRACT

Disclosed herein are compositions comprising NFIA inhibitors, as well as methods of using the same to treat glioma and astrocytomas.

24 Claims, 4 Drawing Sheets

U.S. PATENT DOCUMENTS

| | | | |
|---|---|---|---|
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,371,241 | A | 12/1994 | Brush |
| 5,391,723 | A | 2/1995 | Priest |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,491,133 | A | 2/1996 | Walder et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,527,899 | A | 6/1996 | Froehler |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,332 | A | 10/1996 | Hoogenboom et al. |
| 5,565,350 | A | 10/1996 | Kmiec |
| 5,565,552 | A | 10/1996 | Magda et al. |
| 5,565,555 | A | 10/1996 | Froehler et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci et al. |
| 5,652,355 | A | 7/1997 | Metelev et al. |
| 5,652,356 | A | 7/1997 | Agrawal |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,920 | A | 12/1997 | Altmann et al. |
| 5,700,922 | A | 12/1997 | Cook |
| 5,714,331 | A | 2/1998 | Buchardt et al. |
| 5,719,262 | A | 2/1998 | Buchardt et al. |
| 5,721,218 | A | 2/1998 | Froehler |
| 5,733,743 | A | 3/1998 | Johnson et al. |
| 5,750,692 | A | 5/1998 | Cook et al. |
| 5,763,588 | A | 6/1998 | Matteucci et al. |
| 5,770,713 | A | 6/1998 | Imbach et al. |
| 5,792,608 | A | 8/1998 | Swaminathan et al. |
| 5,792,747 | A | 8/1998 | Schally et al. |
| 5,830,653 | A | 11/1998 | Froehler et al. |
| 5,871,907 | A | 2/1999 | Winter et al. |
| 6,005,096 | A | 12/1999 | Matteucci et al. |
| 6,656,730 | B1 | 12/2003 | Manoharan |
| 7,195,916 | B2 | 3/2007 | Qin et al. |
| 2006/0019256 | A1 * | 1/2006 | Clarke et al. ...................... 435/6 |

FOREIGN PATENT DOCUMENTS

| | | |
|---|---|---|
| EP | 0 173 494 | 3/1986 |
| EP | 0 184 187 | 6/1986 |
| EP | 0 125 023 | 6/1991 |
| WO | WO 86/01533 | 3/1986 |
| WO | WO 87/02671 | 5/1987 |
| WO | WO 89/02468 | 3/1989 |
| WO | WO 89/05345 | 6/1989 |
| WO | WO 89/07136 | 8/1989 |
| WO | WO 90/02809 | 3/1990 |
| WO | WO 91/17271 | 11/1991 |
| WO | WO 92/01047 | 1/1992 |
| WO | WO 92/07573 | 5/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/07883 | 4/1993 |
| WO | WO 93/24510 | 12/1993 |
| WO | WO 94/02610 | 2/1994 |

OTHER PUBLICATIONS

Beerli R R et al. "Intracellular Expression of Single Chain Antibodies Reverts ErbB-2 Transformation." J. Biol. Chem. 269(39):23931-36 (1994).

Beidler C B et al. "Cloning and High Level Expression of a Chimeric Antibody with Specificity for Human Carcinoembryonic Antigen." J. Immunol. 141(11):4053-60 (1988).

Berkner K L. "Development of Adenovirus Vectors for the Expression of Heterologous Genes." Biotechniques 6(7):616-29 (1988).

Better M et al. "*Escherichia coli* Secretion of an Active Chimeric Antibody Fragment." Science 240:1041-43 (1988).

Biocca S et al., "Intracellular Immunization with Cytosolic Recombinant Antibodies." Biotechnology (N.Y.) 12:396-99 (1994).

Biocca S et al., "Expression and targeting of intracellular antibodies in mammalian cells." EMBO J. 9(1):101-08 (1990).
Brown J P et al., "Protein Antigens of Normal and Malignant Human Cells Identified by Immunoprecipitation with Monoclonal Antibodies." J. Biol. Chem. 255(11):4980-83 (1980).
Brown J P et al., "Structural Characterization of Human Melanoma-Associated Antigen p97 With Monoclonal Antibodies." J. Immunol. 127(2):539-46 (1981).
Carlson J R, "A New Means of Inducibly Inactivating a Cellular Protein." Mol. Cell. Biol. 8(6):2638-46 (1988).
Carlson J R, "A new use for intracellular antibody expression: Inactivation of human immunodeficiency virus type 1." Proc. Natl. Acad. Sci. USA 90:7427-28 (1993).
Chen S-Y et al., "Intracellular Antibodies as a New Class of Therapeutic Molecules for Gene Therapy." Hum. Gene Ther. 5:595-601 (1994).
Chen S-Y et al., "Combined intra- and extracellular immunization against human immunodeficiency virus type 1 infection with a human anti-gp120 antibody." Proc. Natl. Acad. Sci. USA 91:5932-36 (1994).
Chowdhury J R et al., "Long-Term Improvement of Hypercholesterolemia After ex Vivo Gene Therapy in LDLR-Deficient Rabbits." Science 254:1802-05 (1991).
Clackson T et al., "Making antibody fragments using phage display libraries." Nature 352:624-28 (1991).
Cole et al. (1985), "The EBV-Hybridoma Technique and its Application to Human Lung Cancer." Monoclonal Antibodies and Cancer Therapy, Alan R. Liss, Inc., pp. 77-96.
Crooke et al., "Pharmacokinetic Properties of Several Novel Oligonucleotide Analogs in mice." J. Pharmacol. Exp. Ther. 277, 923-937 (1996).
Dai Y et al., "Gene therapy via primary myoblasts: Long-term expression of factor IX protein following transplantation in vivo." Proc. Natl. Acad. Sci. USA 89:10892-95 (1992).
Danos O and Mulligan R C, "Safe and efficient generation of recombinant retroviruses with amphotropic and ecotropic host ranges." Proc. Natl. Acad. Sci. USA 85:6460-64 (1988).
Duan L et al., "Potent inhibition of human immunodeficiency virus type 1 replication by an intracellular anti-Rev single-chain antibody." Proc. Natl. Acad. Sci. USA 91:5075-79 (1994).
Eglitis M A et al., "Gene Expression in Mice After High Efficiency Retroviral-Mediated Gene Transfer." Science 230:1395-98 (1985).
Englisch et al., "Chemically Modified Oligonucleotides as Probes and Inhibitors." Angewandte Chemie, International Edition, 30(6):613-629 (1991).
Ferry N et al., "Retroviral-mediated gene transfer into hepatocytes in vivo." Proc. Natl. Acad. Sci. USA 88:8377-81 (1991).
Flotte T R et al., "Gene Expression from Adeno-associated Virus Vectors in Airway Epithelial Cells." Am. J. Respir. Cell. Mol. Biol. 7:349-56 (1992).
Flotte T R et al., "Expression of the Cystic Fibrosis Transmembrane Conductance Regulator from a Novel Adeno-associated Virus Promoter." J. Biol. Chem. 268(5):3781-90 (1993).
Fuchs P et al., "Targeting Recombinant Antibodies to the Surface of *Escherichia coli*: Fusion to a Peptidoglycan Associated Lipoprotein." Biotechnology (N.Y.) 9:1369-72 (1991).
Galfre G et al., "Antibodies to Major Histocompatibility Antigens Produced by Hybrid Cell Lines." Nature 266:550-52 (1977).
Garrard L J et al., "$F_{AB}$ Assembly and Enrichment in a Monovalent Phage Display System." Biotechnology (N.Y.) 9:1373-77 (1991).
Gefter M L et al., "A Simple Method for Polyethylene Glycol-Promoted Hybridization of Mouse Myeloma Cells." Somatic Cell Genet. 3(2):231-36 (1977).
Gram H et al., "In vitro selection and affinity maturation of antibodies from a naïve combinatorial immunoglobulin library." Proc. Natl. Acad. Sci. USA 89:3576-80 (1992).
Griffiths A D et al., "Human anti-self antibodies with high specificity from phage display libraries." EMBO J. 12(2):725-34 (1993).
Haj-Ahmad Y and Graham F L, "Development of a Helper-Independent Human Adenovirus Vector and Its Use in the Transfer of the Herpes Simplex Virus Thymidine Kinase Gene." J. Virol. 57(1):267-74 (1986).
Hawkins R E et al., "Selection of Phage Antibodies by Binding Affinity Mimicking Affinity Maturation." J. Mol. Biol. 226:889-96 (1992).
Hay B N et al., "Bacteriophage cloning and *Escherichia coli* expression of a human IgM Fab." Hum. Antibodies Hybridomas 3:81-85 (1992).
Hermonat P L and Muzyczka N, "Use of adeno-associated virus as a mammalian DNA cloning vector: Transduction of neomycin resistance into mammalian tissue culture cells." Proc. Natl. Acad. Sci. USA 81:6466-70 (1984).
Herz J and Gerard R D, "Adenovirus-mediated transfer of low density lipoprotein receptor gene acutely accelerates cholesterol clearance in normal mice." Proc. Natl. Acad. Sci. USA 90:2812-16 (1993).
Hoogenboom H R et al., "Multi-subunit proteins on the surface of filamentous phage: methodologies for displaying antibody (Fab) heavy and light chains." Nucleic Acids Res. 19(15):4133-37 (1991).
Huber B E et al., "Retroviral-mediated gene therapy for the treatment of hepatocellular carcinoma: An innovative approach for cancer therapy." Proc. Natl. Acad. Sci. USA 88:8039-43 (1991).
Huse W D et al., "Generation of a Large Combinatorial Library of the Immunoglobulin Repertoire in Phage Lambda." Science 246:1275-81 (1989).
Hwu P et al., "Functional and Molecular Characterization of Tumor-Infiltrating Lymphocytes Transduced with Tumor Necrosis Factor-$\alpha$ cDNA for the Gene Therapy of Cancer in Humans." J. Immunol. 150(9):4104-15 (1993).
Kabanov et al., "A new class of antivirals: antisense oligonucleotides combined with a hydrophobic substituent effectively inhibit influenza virus reproduction and synthesis of virus-specific proteins in MDCK cells." FEBS Lett. 259(2):327-330 (1990).
Kabat E A et al. (1991) Sequences of Proteins of Immunological Interest, Fifth Edition, U.S. Department of Health and Human Services, NIH Publication No. 91-3242.
Karlin S and Altschul S F, "Methods for assessing the statistical significance of molecular sequence features by using general scoring schemes." Proc. Natl. Acad. Sci. USA 87:2264-68 (1990).
Karlin S and Altschul S F, "Applications and statistics for multiple high-scoring segments in molecular sequences." Proc. Natl. Acad. Sci. USA 90:5873-77 (1993).
Kay M A et al., "Hepatic Gene Therapy: Persistent Expression of Human $\alpha$1-Antitrypsin in Mice after Direct Gene Delivery In Vivo." Hum. Gene Ther. 3:641-47 (1992).
R. H. Kennett, In Monoclonal Antibodies: Hybridomas: A New Dimension in Biological Analyses, Plenum Publishing Corp., New York, N.Y. (1980).
Kohler G and Milstein C, "Continuous cultures of fused cells secreting antibody of predefined specificity." Nature 256:495-97 (1975).
Kozbor D and Roder J C, "The production of monoclonal antibodies from human lymphocytes." Immunol. Today 4(3):72-79 (1983).
Lee N S et al., "Expression of small interfering RNAs targeted against hIV-1 *rev* transcripts in human cells." Nature Biotechnol. 20:500-05 (2002).
Lemarchand P et al., "Adenovirus-mediated transfer of a recombinant human $\alpha_1$-antitrypsin cDNA to human endothelial cells." Proc. Natl. Acad. Sci. USA 89:6482-86 (1992).
Lerner E A, "How to Make a Hybridoma." Yale J. Biol. Med., 54:387-402 (1981).
Letsinger et al., "Cholesteryl-conjugated oligonucleotides: Synthesis, properties, and activity as inhibitors of replication of human immunodeficiency virus in cell culture." Proc. Natl. Acad. Sci., 86:6553-6556 (1989).
Liu A Y et al., "Production of a Mouse-Human Chimeric Monoclonal Antibody to CD20 with Potent Fc-Dependent Biologic Activity." J. Immunol. 139(10):3521-26 (1987).
Liu A Y et al., "Chimeric mouse-human IgG1 antibody that can mediate lysis of cancer cells." Proc. Natl. Acad. Sci. USA 84:3439-43 (1987).
Logan J J et al., "Cationic lipids for reporter gene and CFTR transfer to rat pulmonary epithelium." Gene Therapy., 2:38-49 (1995).
Manoharan et al., "Chemical Modifications to Improve Uptake and Bioavailability of Antisense Oligonucleotides." Ann. N.Y. Acad. Sci., 660:306-309 (1992).

Manoharan et al., "Introduction of a Lipophilic Thioether Tether in the Minor Groove of Nucleic Acids for Antisense Applications." Bioorg. Med. Chem. Let., 3(12):2765-2770 (1993).
Manoharan et al., "Cholic Acid-Oligonucleotide Conjugates for Antisense Applications." Bioorg. Med. Chem. Let., 4(8):1053-1060 (1994).
Manoharan et al., "Oligonucleotide Conjugates: Alteration of the Pharmacokinetic Properties of Antisense Agents." Nucleosides & Nucleotides, 14(3-5):969-973 (1995).
Manoharan et al., "Lipidic Nucleic Acids." Tetrahedron Lett., 36(21):3651-3654 (1995).
Marasco W A et al., "Design, intracellular expression, and activity of a human anti-human immunodeficiency virus type 1 gp120 single-chain antibody." Proc. Natl. Acad. Sci. USA 90:7889-93 (1993).
Martin et al., "A New Access to 2'-*O*-Alkylated Ribonucleosides and Properties of 2'-*O*-Alkylated Oligoribonucleotides." Helv. Chim. Acta, 78:486-504 (1995).
McCafferty J et al., "Phage antibodies: filamentous phage displaying antibody variable domains." Nature 348:552-54 (1990).
McLaughlin S K et al., "Adeno-Associated Virus General Transduction Vectors: Analysis of Proviral Structures." J. Virol. 62(6):1963-73 (1988).
Mhashilkar A M et al., "Inhibition of HIV-1 Tat-mediated LTR transactivation and HIV-1 infection by anti-Tat single chain intrabodies." EMBO J. 14(7):1542-51 (1995).
Miller A D, "Progress Toward Human Gene Therapy." Blood 76(2):271-78 (1990).
Mishra et al., "Improved leishmanicidal effect of phosphorotioate antisense oligonucleotides by LDL-mediated delivery." Biochim. Biophys. Acta, 1264:229-237 (1995).
Morrison S L, "Transfectomas Provide Novel Chimeric Antibodies." Science 229:1202-07 (1985).
Muzyczka N, "Use of Adeno-Associated Virus as a General Transduction Vector for Mammalian Cells." Curr. Top. Microbiol. Immunol. 158:97-129 (1992).
Myers E W and Miller W, "Optimal alignments in linear space." Comput. Appl. Biosci. 4(1):11-17 (1988).
Neves et al. "Disruption of the murine nuclear factor I-A gene (Nfia) results in perinatal lethality, hydrocephalus, and agenesis of the corpus callosum." Proc. Nat. Acad. Sci. USA. 96(21):11946-11951 (1999).
Nielsen et al., "Sequence-Selective Recognition of DNA by Strand Displacement with a Thymine-Substituted Polyamide." Science, 254:1497-1500 (1991).
Nishimura Y et al., "Recombinant Human-Mouse Chimeric Monoclonal Antibody Specific for Common Acute Lymphocytic Leukemia Antigen." Cancer Res. 47:999-1005 (1987).
Oberhauser et al., "Effective incorporation of 2'-O-methyl-oligoribonucleotides into liposomes and enhanced cell association through modification with thiocholesterol." Nucl. Acids Res., 20(3):533-538 (1992).
Pearson W R and Lipman D J, "Improved tools for biological sequence comparison." Proc. Natl. Acad. Sci. USA 85:2444-48 (1988).
Qin et al. (2003) "Inhibiting HIV-1 infection in human T cells by lentiviral-mediated delivery of small interfering RNA against CCR5." Proc. Nat. Acad. Sci. USA 100(1):183-188.
Quantin B et al., "Adenovirus as an expression vector in muscle cells in vivo." Proc. Natl. Acad. Sci. USA 89:2581-84 (1992).
Richardson J H et al., "Phenotypic knockout of the high-affinity human interleukin 2 receptor by intracellular single-chain antibodies against the α subunit of the receptor." Proc. Natl. Acad. Sci. USA 92:3137-41 (1995).
Rosenfeld M A et al., "In Vivo Transfer of the Human Cystic Fibrosis Transmembrane Conductance Regulator Gene to the Airway Epithelium." Cell 68:143-55 (1992).
Rosenfeld M A et al., "Adenovirus-Mediated Transfer of a Recombinant α1-Antitrypsin Gene to the Lung Epithelium in Vivo." Science 252:431-34 (1991).
Saison-Behmoaras et al., "Short modified antisense oligonucleotides directed against Ha-*ras* point mutation induce selective cleavage of the mRNA and inhibit T24 cells proliferation." EMBO J. 10(5):1111-1118 (1991).
Samulski R J et al., "Helper-Free Stocks of Recombinant Adeno-Associated Viruses: Normal Integration Does Not Require Viral Gene Expression." J. Virol. 63(9):3822-28 (1989).
San H et al., "Safety and Short-Term Toxicity of a Novel Cationic Lipid Formulation for Human Gene Therapy." Human Gene Therapy 4:781-88 (1993).
Sanghvi, Y. S., "Heterocyclic Base Modifications in Nucleic Acids and Their Applications in Antisense Oligonucleotides." Antisense Research and Applications, Crooke, S. T. And Lebleu, B. ed., CRC Press, Boca Raton, Chp. 15, pp. 273-288 (1993).
Sanghvi, Y. S., "Oligoribonucleotides." Antisense Research and Applications, Crooke, S. T. and Lebleu, B. ed., CRC Press, Boca Raton, Chp. 16, pp. 289-301 (1993).
Shaw D R et al., "Mouse/Human Chimeric Antibodies to a Tumor-Associated Antigen: Biologic Activity of the Four Human IgG Subclasses." J. Natl. Cancer Inst. 80(19):1553-59 (1988).
Shea et al., "Synthesis, hybridization properties and antiviral activity of lipid-oligodeoxynucleotide conjugates." Nucl. Acids Res. 18(13):3777-3783 (1990).
Sui G et al., "A DNA vector-based RNAi technology to suppress gene expression in mammalian cells." Proc. Natl. Acad. Sci. USA 99(8):5515-20 (2002).
Sun L K et al., "Chimeric antibody with human constant regions and mouse variable regions directed against carcinoma-associated antigen 17-1A." Proc. Natl. Acad. Sci. USA 84:214-18 (1987).
Svinarchuk et al., "Inhibition of HIV proliferation in MT-4 cells by antisense oligonucleotide conjugated to lipophilic groups." Biochimie. 75:49-54 (1993).
The Concise Encyclopedia of Polymer Science and Engineering, "Polynucleotides," pp. 858-859, Kroschwitz, J. I., ed. John Wiley & Sons, 1990.
Torelli A and Robotti C A, "Advance and Adam: two algorithms for the analysis of global similarity between homologous informational sequences." Comput. Appl. Biosci. 10(1):3-5 (1994).
Tratschin J D et al., "Genetic Analysis of Adeno-Associated Virus: Properties of Deletion Mutants Constructed In Vitro and Evidence for an Adeno-Associated Virus Replication Function." J. Virol. 51(3):611-619 (1984).
Tratschin J D et al., "A Human Parvovirus, Adeno-Associated Virus, as a Eucaryotic Vector: Transient Expression and Encapsidation of the Procaryotic Gene for Chloramphenicol Acetyltransferase." Mol. Cell. Biol. 4(10):2072-81 (1984).
Tratschin J D et al., "Adeno-Associated Virus Vector for High-Frequency Integration, Expression, and Rescue of Genes in Mammalian Cells." Mol. Cell. Biol. 5(11):3251-60 (1985).
van Beusechem V W et al., "Long-term expression of human adenosine deaminase in rhesus monkeys transplanted with retrovirus-infected bone-marrow cells." Proc. Natl. Acad. Sci. USA 89:7640-44 (1992).
Verhoeyen M et al., "Reshaping Human Antibodies : Grafting an Antilysozyme Activity." Science 239:1534-36 (1988).
Werge T M et al., "Intracellular immunization—Cloning and intracellular expression of a monoclonal antibody to the $p21^{ras}$ protein." FEBS Lett. 274(1,2):193-98 (1990).
Wilbur W J and Lipman D J, "Rapid similarity searches of nucleic acid and protein data banks." Proc. Natl. Acad. Sci. USA 80:726-30 (1983).
Wilson J M et al., "Hepatocyte-directed Gene Transfer in Vivo Leads to Transient Improvement of Hypercholesterolemia in Low Density Lipoprotein Receptor-deficient Rabbits." J. Biol. Chem. 267(2):963-67 (1992).
Wilson J M et al., "Retrovirus-mediated transduction of adult hepatocytes." Proc. Natl. Acad. Sci. USA 85:3014-18 (1988).
Wolff J A et al., "Direct Gene Transfer into Mouse Muscle in Vivo." Science 247:1465-68 (1990).

Wondisford F E et al., "Cloning of the Human Thyrotropin β-Subunit Gene and Transient Expression of Biologically Active Human Thyrotropin after Gene Transfection." Mol. Endocrinol. 2(1):32-39 (1988).
Wood C R et al., "The synthesis and in vivo assembly of functional antibodies in yeast." Nature 314:446-49 (1985).
Wu G Y and Wu C H, "Receptor-mediated Gene Delivery and Expression in Vivo." J. Biol. Chem. 263(29):14621-14624 (1988).
Yeh M Y et al., "A Cell-Surface Antigen which is Present in the Ganglioside Fraction and Shared by Human Melanomas." Int. J. Cancer 29:269-275 (1982).
Yeh M Y et al., "Cell surface antigens of human melanoma identified by monoclonal antibody." Proc. Natl. Acad. Sci. USA 76(6):2927-31 (1979).

* cited by examiner

FIGURE 4A-D
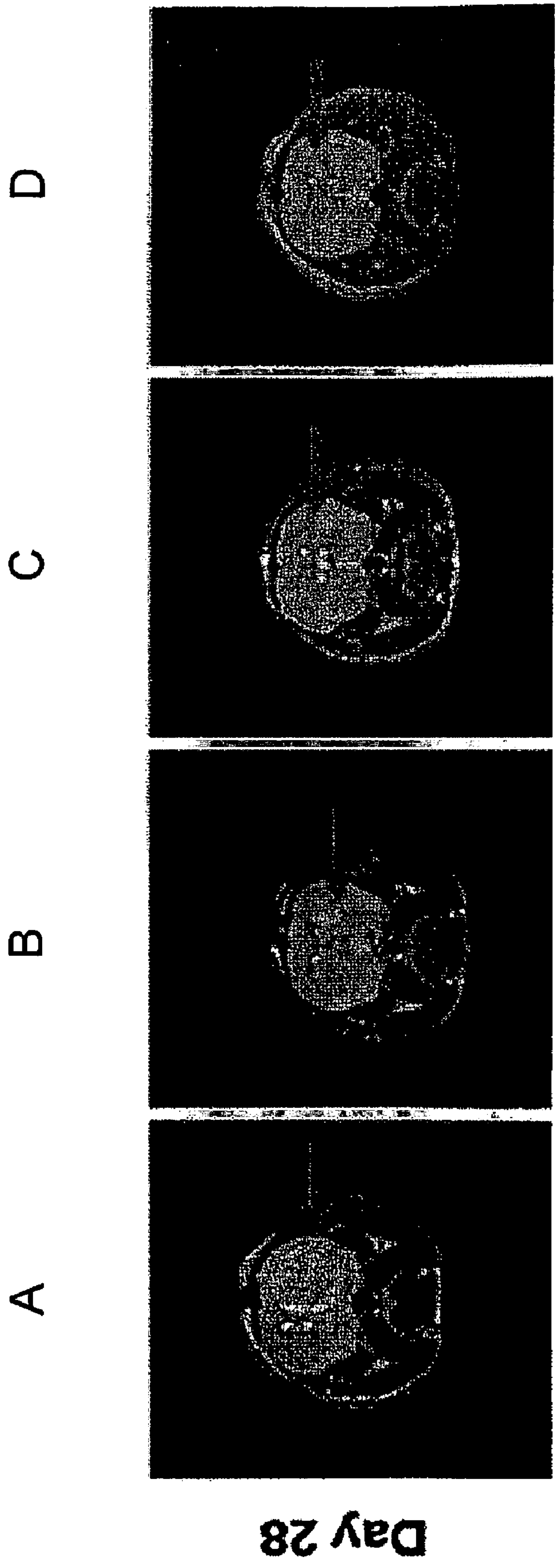

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: NFIA antisense oligonucleotide

<400> SEQUENCE: 1

gaggcacatg gagaactaaa                                                20


<210> SEQ ID NO 2
<211> LENGTH: 20
<212> TYPE: DNA
<213> ORGANISM: Artificial Sequence
<220> FEATURE:
<223> OTHER INFORMATION: NFIA antisense oligonucleotide

<400> SEQUENCE: 2

gatgcacgtg aagacgtata                                                20


<210> SEQ ID NO 3
<211> LENGTH: 9407
<212> TYPE: DNA
<213> ORGANISM: Homo sapien

<400> SEQUENCE: 3

ggccgcggag gctcgggacc cggctggccg cgcggcgccg cagccgcccc ctccccccaca    60

ccccctcccc cccgcggcgg cggcgcgagc gggcggcggc tgtgcggtgc ggtgcagagc   120

ggaggcggag gcgggcgcgc gggcagctcg cgggcacccg gccgggccgg cgcgggagcg   180

ggaaagggtg cgctatgcct ttaacacccg cgtacagtag gcatgtatag tggagtgtag   240
```

-continued

```
ggaaactcta ggcggggtta aagttcagct catggagcgg caatagcgct ggctggctgg    300
ctgcagttga gccgacttgg aaatgtgaac gcaagaagca ggcttgattt tttttctcc    360
cccttctct ctctctctct ctctctctct tcctctctcc ctctttctcc tctctcaccc    420
acactcacgc acacctccaa accgcacacc cagacgcaca cgcatacccc agcgcccggc    480
agttatgtat tctccgctct gtctcaccca ggatgaattt catcctttca tcgaagcact    540
tctgccccac gtccgagcct ttgcctacac atggttcaac ctgcaggccc gaaaacgaaa    600
atacttcaaa aaacatgaaa agcgtatgtc aaaagaagaa gagagagccg tgaaggatga    660
attgctaagt gaaaaaccag aggtcaagca gaagtgggca tctcgacttc tggcaaagtt    720
gcggaaagat atccgacccg aatatcgaga ggattttgtt cttacagtta cagggaaaaa    780
acctccatgt tgtgttcttt ccaacccaga ccagaaaggc aagatgcgaa gaattgactg    840
cctccgccag gcagataaag tctggaggtt ggaccttgtt atggtgattt tgtttaaagg    900
tattccgctg gaaagtactg atggcgagcg ccttgtaaag tccccacaat gctctaatcc    960
agggctctgt gtccaacccc atcacatagg ggtttctgtt aaggaactcg atttatattt   1020
ggcatacttt gtgcatgcag cagattcaag tcaatctgaa agtcccagcc agccaagtga   1080
cgctgacatt aaggaccagc cagaaaatgg acatttgggc ttccaggaca gttttgtcac   1140
atcaggtgtt tttagtgtca ctgagctagt aagagtgtca cagacaccaa tagctgcagg   1200
aactggccca aatttttctc tctcagattt ggaaagttct tcatactaca gcatgagtcc   1260
aggagcaatg aggaggtctt tacccagcac atcctctacg agctccacaa agcgcctcaa   1320
gtctgtggag gatgaaatgg acagtcctgg tgaggagcca ttttatacag gccaagggcg   1380
ctccccagga agtggcagtc agtcaagtgg atggcatgaa gtggagccag gaatgccatc   1440
tccaaccaca ctgaagaagt cggagaagtc tggtttcagc agcccctccc cttcacagac   1500
ctcctccctg ggaacggcgt tcacacagca tcaccgacct gtcattacag gacccagagc   1560
aagtccgcat gcaacaccat cgactcttca tttcccgaca tcacccatta tccagcagcc   1620
tgggccttac ttctcacacc cagccatccg ctatcaccct caggagacgc tgaaagaatt   1680
tgtccaactt gtctgccctg atgctggtca gcaggctgga caggtggggt tcctcaatcc   1740
caatgggagc agccaaggca aggtgcacaa cccattcctt cccaccccaa tgttgccacc   1800
gccaccgcca ccaccgatgg ccaggcctgt gcctctgccg gtgccagaca caaagcctcc   1860
aaccacgtca acagaaggag gtgcagcctc ccccacgtca ccaatcctgg tacctgggat   1920
aaaagttgca gcgtcccacc atccaccaga cagaccacct gaccccttct caactctgta   1980
acatggacgc aacctcaacc cagcgcagtt acaacttcac tatcagcgga aggggagaaa   2040
aaccgattca aatcaacttg tacatggaaa cagcaagcat tatggtcaaa cagcaaaggc   2100
cataaccttt tgggattttt ttttttttaa aatactttag ggactgttgt aatttctcat   2160
atggtgctgg aaatggttgg gctttgtaac atttgaagtg tttccatggt agcgtgagca   2220
ttaggtgacg tggctagcgg aggactaccc ttgctcactg acttcctgtt gtaacacact   2280
ttccttacgg agcctggctg tttcacagta tttcatgaat ttacccacac aggtgtgatc   2340
ctccttgagc attgaggagg cacatggaga actaaatctt ttgtagtagc tgagatctgc   2400
aatatataac gggacagtca aagggcaatg tttttctgta acatattgga aaaagaaaat   2460
gcagttatat tcctttttta tttgttcctt tagtttgttt tggttcagca gtcagcagtt   2520
aagtatataa catggcccgc aaggacaatg aatccactca cattgcagaa caattccgaa   2580
aatggcaaac tactactact actgttcagt tttttaaaag ttttgaaatg ctgcacttac   2640
```

-continued

```
atttaaaaaa acaacaacaa cattttttca acaatttcaa caatgacaca aaaattcaca   2700
tggaaatggg gaagatggtc tgttttgaca gaaactgaca ggaatcaatc aaaacaatcg   2760
aattttgaat tgagtaaagt gcaatttcat tggatagcta aatatctttg taagatagag   2820
attgttgaaa attctatttt tgtttttcta gtcctttcac cccaggactc taaattattg   2880
gggtaaaaaa cagccttgca agaaaaaggg gagctatttt tgctttttat gtttttttatt  2940
gttaaacttg tatcccttta aaaactgaag gaaattaaaa aaaaaaaaca aaaaaacaaa   3000
tctaatggtg cttttaccac aatatgttaa ctacattaaa tgctaattaa ttattttctg   3060
ttatcaaagc acatgactaa aatgaaatca tggtatctgt taattttata agctagaagt   3120
cactataatg gattacgcca attctaaaaa attttacacc tatctggcat cataggattt   3180
atcagttatc agacacctca ttgtaccaga gattgtccag aagttttaaa gacctttgca   3240
tccctgaact gggctatggg aaataataat agtaataata ataataataa taatgatgaa   3300
accaatactg acacaaatgc tggtgcccat tcagatcaag ggtacttgtt agggaaaaaa   3360
aaaaaagttt gcacccccaa acgtcctgta tcttatgaaa aaaaaaacaa aaaacaaaaa   3420
caaaaaaaaa acacaaaaaa ccacagaaac aaaaacaaaa aaaagtgcaa gtgatttttc   3480
taccagacag cgaagcaccc ctttgcttcc catgcgactt caagaaggtt tcctatacta   3540
tacatatata tacgttctgg ttggcaagcc ctgctgatca gagaaagtct ctgcatgttc   3600
tagtgttagt aactaatttt tatatagtta atgtaggata aagtagagtg cattaagaca   3660
caatattgta atccctactc taggcacttg cctttaaact atgtttttca gcccttcaga   3720
agggttctac tactgtccta tacaatcaag taactgaaat tcttgggaag acactttgct   3780
cctcatcttt ctccccgaaa caatgttgtt ttgttttgtt ttttttcctt aatttgcacg   3840
aaaacaaaaa ttccatatca atgtgccttg ccctggatag cgattatttg tggaattgtt   3900
gcacatgctc ctctattgaa agggttttt ccctagtcaa gcatttggag acacttttttg   3960
taaatgtgac ttttatgtca gccatcgtca gtttcaacat ctagaactaa atagaaagct   4020
agttgttccg cagataggag tagtctttat tgtcctgtac ggtcggtggc agtgctattc   4080
tgagatctgt agatgcttag aatatcagta ttttggatgt tgctgcattt tacaatttat   4140
ttggagtctt cctttatttt cccccagata tatgaaaata tgcaatacct gcttatatca   4200
tgtagaaaag cttagcaatt attaattttt cttttatttt tttttatttg accaaagtcg   4260
gtgctgcact tgacgcagtg tgttttaggt gtttgtcttt gtactttttt gtgatttttg   4320
aatgcacgtg cgcaggaagg gctcctctta gagaagcagt caaactgtga agcactaagc   4380
tgaccctgct tcaagcaatt ttgtttttac aactgttcct ttcacaagca agccttaaaa   4440
aaaaaaaaga caacttcctt tttcttcagc tcccacaccc cattttcttt agcagactgc   4500
agtcaatcca cattcaataa aaagtatata atgcccattt ttatatgcac gtttttaaac   4560
ttccaagttc tgaaaattgt ttactggtta tctctattta aggaaaaaaa aataaaataa   4620
aacattttgg attttcatat gtgtctgata agtggttgaa tagtcgtttg gcgctgttgt   4680
atggtgtgat tgtcagtgta tggtgtcact tcctatagcc agccagcata ctttgccttc   4740
ccctatagca cttagctggg cattacttta ttatgacata tgtgcactaa aaaatgaaaa   4800
aaaggaaaaa aagaaaaaaa aaaagaaaaa atagcagctt tcagtgcttc acagtgaagg   4860
gaaaaaagcc tagacaaaca ttttgtcaga accttgcaat aagccaaggt attaccagta   4920
aattggttgt atatacaata aaattgcacc cttttttaaa caaaacaaac taagcaatag   4980
tttgggcagt tttagttgtt tttagtgagc atgttgtagt catgactgca aagagagaga   5040
```

-continued

```
ataaactgcc cgctcagaag atatgtaatt tgtattgttg tatagtttta ttgattacac   5100
tgatttattc taccctattt tataatgcag gacttttgta atgttgttta aatgaggaaa   5160
aatttctgtc aaattagcct agtaaaattt ctgatcgttc attataaagg cagcgttcat   5220
agaattgctt ttctttcttt ttaccccccc tttgggaact ggatttaagt ttaaaacttt   5280
cctgtttcct tttttttttt ttttttgtaa gtatttaaat acaattattt ttttctctca   5340
atggtatagc atattcctat gcttgagaag tataggtcta ctgaaaaacc attgtaaatg   5400
gacgttacag gtatgctgta tttttgaagg tattttgttg tattaagttt gatgaagcta   5460
aaattaggga actctgaaca gatttgcagg aaaaaatgtt ttaaaggctt taaaacatta   5520
gggaggcagt ctagggtgat aacgaacagg ggttaagtat taaatacacg aagttacatt   5580
tttgttcatg tttcattgtc cagaaagcag caggaaacta ttcagttgtg atcaagcagg   5640
aaaaaagaaa caccaacagt tgccagtgtt tttgcttttt agcttaaaag catagtgaag   5700
atgcttgagg aagactttgc tacctggggt gtgtagacag acagactgag agctatcagc   5760
atttgaaggc ccagcccttg actctgagac acatttgaat tttttctttc ccatcaaatg   5820
gcattaacaa gattgggcaa agatgagtcc ctcaaatttc tgtgtttttt gtttgtttgt   5880
ttgtttgttt tttctttggg aactgaagtc agaggcacga acactaactc ttagcatttt   5940
tctgtagact ttttcttctg gcccttgtcc ctgccagcaa aacgcccctt ttctgatcat   6000
tcgtgcgcag agggcctccc agtaatgcca cgctctccat gctagagagc cttctctttc   6060
ctctgaggtt tgaactgatg ttctgtgtct tcacaccctg gcatgacagt tacgtgtggt   6120
cagcccgctc cccaggcccg tccctgccgc cgccaggtgt gggctctagg caggccgaca   6180
aggttacacc tcccagagct tgtgatcttc attttctgac agtcaaagtg tgaaggaacc   6240
cagacttccc cgagccacgg tgttcagtca gcccacagga atatgcaaga cccatctcca   6300
aaagtttgtc tttgattttt tccaagccct tagccccata agctttgaat cctgtagtta   6360
cagtggcata aaggactgac aaaacctgga taaggaaaaa cctttttttt ctatgaattt   6420
tttttgtttt ttaggggaaa gggattctaa gaatgtcatt taatgtactt tgcatcatgt   6480
ctctagaaat atctttgtcc atagtggtgg tggagtctct ctctctctct ctctttttgt   6540
ttgcttctgt tttctttctt gtcttcattc tttcttttct tttttatttc tggtagcagg   6600
cctccataga acaaatctaa aacacaacca ccatagtaat gtaaggagag cttcagtggc   6660
acctcaaaac ccacccttcg agatctgtcc aaagacagtc tcagaaagct gcactgccca   6720
ccggctcagc tttcattcaa aaaggcttcc aaggccaatt ctgtcttgaa gtcaatgcat   6780
gtatttactg tttgacagta aacccgctct gccttctcca cgtccaaggc tgtgcattcg   6840
tctaattagc gtcgtgtatg ttttcctttt atttttttcca ataaaaaagc agtgggatga   6900
aaattgcttt gatatatagc aggtaacatt gaagctattc catagcactt aactgtagtg   6960
aatactgtgt caccaatttt gaaatcaatt taatgtttaa tgcaaatcca ttacatggtg   7020
ctattatagg ctgacaaaat gatttacaca aatgtgacaa cttgggctca attcactctg   7080
ctttccaaca gtgtaaatgc atagcagtgt ttatctgcat gagaactatg cactaatcta   7140
tctgaagaaa aaaactatat caactttggt atctactttc cgtttacttc aatccttgcc   7200
tttttggtca ttgttataat gccagcttta ggacagaaag aattataaga aaaccagcat   7260
aatacctgat atattaaaat gtagtgcctg tgaaatctgt attatattgc tcttctgaag   7320
taagattttt ctacaccggt agccttcgct gtctgtcagt caggaccttc tggtataggt   7380
gatgtaaaat aaccgtacaa tattaatgca tgcgattcca taatgcttag tgaactgtat   7440
```

-continued

```
gaatattact caaagttatg ttagtctttt tttccgactt ggttcttgtc agctaggttt   7500

aaaggtattt cactgagaac gcaaattctg tcttttcttg atttcggctg ttttcagtat   7560

tttggaggta tacatttact taaattcagt attactcgtg ttttgttttt gtttttgttt   7620

tttgttttct ttttcctagg ggacaagcat gggtgtttga tttcagaaat cagtacctgg   7680

cgagattttt gtctcaaaac gactatttga atttcaagaa ctgtgctgcg aagacactct   7740

gagaacattt gcaagtcagg ggcattttcc ttgacccttg actgatgcta tgcggagact   7800

gatacatttt cttaatggac aatgttcaag ccaggtaccc atgcttgatc tgtcttcaca   7860

ccagacctcc tcatattaaa aggaaaaata agaaaaaaaa tgtaagaaat cacatggcta   7920

tttagtttca tgcacagttg caatattttc ttcaaaaata aaactctgta caaactttgg   7980

gcccgattca taagaaaaag aagtttgcta ttaacacggg attttttaa tatacttttt   8040

ttggtctaaa tttgaaatta cttgcttccc aaattaaata aatttcatct cattttttc   8100

cctaaaccag cacccatctg ccttttattc cccaaagagt tacctttccc agattagggg   8160

gatggtatgt ggggagcaga tagcggaaat gcttagaaag ataaggggga ccacccacag   8220

ctggtcgtga gaacagggag acagtgtgtg ggggtgggac ctcatctgtg tgcctggtat   8280

cctgagtttt acatgtagat gcattcgcct atttgattca gaaaaataaa ctttcccaaa   8340

atgtgtctga accacaagag catacagtgg aagtgctacc tctaatctaa ccagagcacc   8400

ttcatggtgg aagacaccca ccaggtcata caatgtgaac ttttgtatct ctgcagtggt   8460

ttcaaggaca aatagtgtcc aatgtattgg gccatttttc ctgctgtttt tatactcaac   8520

ttctcaaaat gaaaaaagct tttattttc ctttgactta tttgtgttgt tcttattttt   8580

taaattttta ttttttgata atagtctgta agttagcctt tttgggtttt ttttttttt   8640

ttttggcttt tttttttgtt tgttttttt tcttttgaca ttgcaaccga aggtcataag   8700

gccgctagct ccgctgggac agaggcttga gagaactaac ggctcggtgc cttctccctg   8760

gtctcagacc atcgtctctg cactgcgaag gcatttggta gcctcgccac tgagatacta   8820

actagaccta gactaggagc tttatcaggt tctaggaggt cctttaggaa gactctcaaa   8880

ggcaaatccc tgatcccccg ccccaccctt agccctgccc tctcaccaga gcaaaattca   8940

ctggggactt ttcccaccac acatggaaat ctgtccactc ggaatacctc tgttttccat   9000

ttcaaattgt agggggaggg gatggaacac ttccagtgat ggtaagagat ctgttatgaa   9060

acgaaacacc ccccgtgtta ataacttggt ctgaaatctg tttttatgag ccgggccccc   9120

tgtgcctcta gtatacttgt attgactctc atagttaccc ttttagtttt actgtgttct   9180

gtgaaaattt gtaattggtt gagaatcact gtgggcgtcc attcttattc aactaaatct   9240

ccacaggttt tttgagctgg tgtggattag tttaactctt gtattcaacc attagtgcta   9300

ccaccttctc acattacaat acaattactg gaagcaagta ctgcatttcc tatgcaacaa   9360

aaaaggaaaa ataaaaaatt gctaatgcta aaaaaaaaaa aaaaaaa                 9407
```

<210> SEQ ID NO 4
<211> LENGTH: 9499
<212> TYPE: DNA
<213> ORGANISM: Homo sapien

<400> SEQUENCE: 4

```
ggccgcggag gctcgggacc cggctggccg cgcggcgccg cagccgcccc ctcccccaca     60

ccccctcccc cccgcggcgg cggcgcgagc gggcggcggc tgtgcggtgc ggtgcagagc    120

ggaggcggag gcgggcgcgc gggcagctcg cgggcacccg gccgggccgg cgcgggagcg    180
```

-continued

```
ggaaagggtg cgctatgcct ttaacacccg cgtacagtag gcatgtatag tggagtgtag    240
ggaaactcta ggcggggtta aagttcagct catggagcgg caatagcgct ggctggctgg    300
ctgcagttga gccgacttgg aaatgtgaac gcaagaagca ggcttgattt tttttctcc     360
cccttctct ctctctctct ctctctctct tcctctctcc ctctttctcc tctctcaccc    420
acactcacgc acacctccaa accgcacacc cagacgcaca cgcatacccc agcgcccggc    480
agttatgtat tctccgctct gtctcaccca ggatgaattt catcctttca tcgaagcact    540
tctgccccac gtccgagcct ttgcctacac atggttcaac ctgcaggccc gaaaacgaaa    600
atacttcaaa aaacatgaaa agcgtatgtc aaaagaagaa gagagagccg tgaaggatga    660
attgctaagt gaaaaaccag aggtcaagca gaagtgggca tctcgacttc tggcaaagtt    720
gcggaaagat atccgacccg aatatcgaga ggattttgtt cttacagtta cagggaaaaa    780
acctccatgt tgtgttcttt ccaacccaga ccagaaaggc aagatgcgaa gaattgactg    840
cctccgccag gcagataaag tctggaggtt ggaccttgtt atggtgattt tgtttaaagg    900
tattccgctg gaaagtactg atggcgagcg ccttgtaaag tccccacaat gctctaatcc    960
agggctctgt gtccaacccc atcacatagg ggtttctgtt aaggaactcg atttatattt   1020
ggcatacttt gtgcatgcag cagattcaag tcaatctgaa agtcccagcc agccaagtga   1080
cgctgacatt aaggaccagc cagaaaatgg acatttgggc ttccaggaca gttttgtcac   1140
atcaggtgtt tttagtgtca ctgagctagt aagagtgtca cagacaccaa tagctgcagg   1200
aactggccca aatttttctc tctcagattt ggaaagttct tcatactaca gcatgagtcc   1260
aggagcaatg aggaggtctt tacccagcac atcctctacg agctccacaa agcgcctcaa   1320
gtctgtggag gatgaaatgg acagtcctgg tgaggagcca ttttatacag gccaagggcg   1380
ctccccagga agtggcagtc agtcaagtgg atggcatgaa gtggagccag gaatgccatc   1440
tccaaccaca ctgaagaagt cggagaagtc tggtttcagc agcccctccc cttcacagac   1500
ctcctccctg ggaacggcgt tcacacagca tcaccgacct gtcattacag gacccagagc   1560
aagtccgcat gcaacaccat cgactcttca tttcccgaca tcacccatta tccagcagcc   1620
tgggccttac ttctcacacc cagccatccg ctatcaccct caggagacgc tgaaagaatt   1680
tgtccaactt gtctgccctg atgctggtca gcaggctgga caggtggggt tcctcaatcc   1740
caatgggagc agccaaggca aggtgcacaa cccattcctt cccaccccaa tgttgccacc   1800
gccaccgcca ccaccgatgg ccaggcctgt gcctctgccg gtgccagaca caaagcctcc   1860
aaccacgtca acagaaggag gtgcagcctc ccccacgtca ccaacctact cgacacccag   1920
cacctccccc gcaaaccgat tcgtcagtgt tggaccacgg gatccaagct ttgtaaatat   1980
ccctcaacag acacagtcct ggtacctggg ataaaagttg cagcgtccca ccatccacca   2040
gacagaccac ctgacccctt ctcaactctg taacatggac gcaacctcaa cccagcgcag   2100
ttacaacttc actatcagcg gaaggggaga aaaaccgatt caaatcaact tgtacatgga   2160
aacagcaagc attatggtca aacagcaaag gccataacct tttgggattt ttttttttt    2220
aaaatacttt agggactgtt gtaatttctc atatggtgct ggaaatggtt gggctttgta   2280
acatttgaag tgtttccatg gtagcgtgag cattaggtga cgtggctagc ggaggactac   2340
ccttgctcac tgacttcctg ttgtaacaca ctttccttac ggagcctggc tgtttcacag   2400
tatttcatga atttacccac acaggtgtga tcctccttga gcattgagga ggcacatgga   2460
gaactaaatc ttttgtagta gctgagatct gcaatatata acgggacagt caaagggcaa   2520
tgtttttctg taacatattg gaaaaagaaa atgcagttat attccttttt tatttgttcc   2580
```

-continued

```
tttagtttgt tttggttcag cagtcagcag ttaagtatat aacatggccc gcaaggacaa   2640
tgaatccact cacattgcag aacaattccg aaaatggcaa actactacta ctactgttca   2700
gtttttaaa agttttgaaa tgctgcactt acatttaaaa aaacaacaac aacatttttt   2760
caacaatttc aacaatgaca caaaaattca catggaaatg gggaagatgg tctgttttga   2820
cagaaactga caggaatcaa tcaaaacaat cgaattttga attgagtaaa gtgcaatttc   2880
attggatagc taaatatctt tgtaagatag agattgttga aaattctatt tttgtttttc   2940
tagtcctttc accccaggac tctaaattat tggggtaaaa aacagccttg caagaaaaag   3000
gggagctatt tttgcttttt atgtttttta ttgttaaact tgtatccctt taaaaactga   3060
aggaaattaa aaaaaaaaaa caaaaaaaca aatctaatgg tgcttttacc acaatatgtt   3120
aactacatta aatgctaatt aattattttc tgttatcaaa gcacatgact aaaatgaaat   3180
catggtatct gttaatttta taagctagaa gtcactataa tggattacgc caattctaaa   3240
aaattttaca cctatctggc atcataggat ttatcagtta tcagacacct cattgtacca   3300
gagattgtcc agaagtttta aagacctttg catccctgaa ctgggctatg ggaaataata   3360
atagtaataa taataataat aataatgatg aaaccaatac tgacacaaat gctggtgccc   3420
attcagatca agggtacttg ttagggaaaa aaaaaaaagt ttgcaccccc aaacgtcctg   3480
tatcttatga aaaaaaaaac aaaaaacaaa aacaaaaaaa aaacacaaaa aaccacagaa   3540
acaaaaacaa aaaaaagtgc aagtgatttt tctaccagac agcgaagcac ccctttgctt   3600
cccatgcgac ttcaagaagg tttcctatac tatacatata tatacgttct ggttggcaag   3660
ccctgctgat cagagaaagt ctctgcatgt tctagtgtta gtaactaatt tttatatagt   3720
taatgtagga taaagtagag tgcattaaga cacaatattg taatccctac tctaggcact   3780
tgcctttaaa ctatgttttt cagcccttca gaagggttct actactgtcc tatacaatca   3840
agtaactgaa attcttggga agacactttg ctcctcatct ttctccccga aacaatgttg   3900
ttttgttttg ttttttttcc ttaatttgca cgaaaacaaa aattccatat caatgtgcct   3960
tgccctggat agcgattatt tgtggaattg ttgcacatgc tcctctattg aaaggggttt   4020
ttccctagtc aagcatttgg agacactttt tgtaaatgtg acttttatgt cagccatcgt   4080
cagtttcaac atctagaact aaatagaaag ctagttgttc cgcagatagg agtagtcttt   4140
attgtcctgt acggtcggtg gcagtgctat tctgagatct gtagatgctt agaatatcag   4200
tattttggat gttgctgcat tttacaattt atttggagtc ttcctttatt ttcccccaga   4260
tatatgaaaa tatgcaatac ctgcttatat catgtagaaa agcttagcaa ttattaattt   4320
ttcttttatt ttttttatt tgaccaaagt cggtgctgca cttgacgcag tgtgttttag   4380
gtgtttgtct ttgtactttt ttgtgatttt tgaatgcacg tgcgcaggaa gggctcctct   4440
tagagaagca gtcaaactgt gaagcactaa gctgaccctg cttcaagcaa ttttgttttt   4500
acaactgttc ctttcacaag caagccttaa aaaaaaaaaa gacaacttcc tttttcttca   4560
gctcccacac cccatttttc ttagcagact gcagtcaatc cacattcaat aaaaagtata   4620
taatgcccat ttttatatgc acgtttttaa acttccaagt tctgaaaatt gtttactggt   4680
tatctctatt taaggaaaaa aaaataaaat aaaacatttt ggattttcat atgtgtctga   4740
taagtggttg aatagtcgtt tggcgctgtt gtatggtgtg attgtcagtg tatggtgtca   4800
cttcctatag ccagccagca tactttgcct tcccctatag cacttagctg ggcattactt   4860
tattatgaca tatgtgcact aaaaaatgaa aaaaaggaaa aaaagaaaaa aaaaaagaaa   4920
aaatagcagc tttcagtgct tcacagtgaa gggaaaaaag cctagacaaa cattttgtca   4980
```

-continued

```
gaaccttgca ataagccaag gtattaccag taaattggtt gtatatacaa taaaattgca   5040
cccttttta aacaaaacaa actaagcaat agtttgggca gttttagttg tttttagtga   5100
gcatgttgta gtcatgactg caaagagaga gaataaactg cccgctcaga agatatgtaa   5160
tttgtattgt tgtatagttt tattgattac actgatttat tctaccctat tttataatgc   5220
aggacttttg taatgttgtt taaatgagga aaaatttctg tcaaattagc ctagtaaaat   5280
ttctgatcgt tcattataaa ggcagcgttc atagaattgc ttttctttct ttttaccccc   5340
cctttgggaa ctggatttaa gtttaaaact ttcctgtttc cttttttttt ttttttttgt   5400
aagtatttaa atacaattat ttttttctct caatggtata gcatattcct atgcttgaga   5460
agtataggtc tactgaaaaa ccattgtaaa tggacgttac aggtatgctg tatttttgaa   5520
ggtattttgt tgtattaagt ttgatgaagc taaaattagg gaactctgaa cagatttgca   5580
ggaaaaaatg ttttaaaggc tttaaaacat tagggaggca gtctagggtg ataacgaaca   5640
ggggttaagt attaaataca cgaagttaca tttttgttca tgtttcattg tccagaaagc   5700
agcaggaaac tattcagttg tgatcaagca ggaaaaaaga aacaccaaca gttgccagtg   5760
tttttgcttt ttagcttaaa agcatagtga agatgcttga ggaagacttt gctacctggg   5820
gtgtgtagac agacagactg agagctatca gcatttgaag gcccagccct tgactctgag   5880
acacatttga attttttctt tcccatcaaa tggcattaac aagattgggc aaagatgagt   5940
ccctcaaatt tctgtgtttt ttgtttgttt gtttgtttgt tttttctttg ggaactgaag   6000
tcagaggcac gaacactaac tcttagcatt tttctgtaga ctttttcttc tggcccttgt   6060
ccctgccagc aaaacgcccc ttttctgatc attcgtgcgc agagggcctc ccagtaatgc   6120
cacgctctcc atgctagaga gccttctctt tcctctgagg tttgaactga tgttctgtgt   6180
cttcacaccc tggcatgaca gttacgtgtg gtcagcccgc tccccaggcc cgtccctgcc   6240
gccgccaggt gtgggctcta ggcaggccga caaggttaca cctcccagag cttgtgatct   6300
tcattttctg acagtcaaag tgtgaaggaa cccagacttc cccgagccac ggtgttcagt   6360
cagcccacag gaatatgcaa gacccatctc caaaagtttg tctttgattt tttccaagcc   6420
cttagcccca taagctttga atcctgtagt tacagtggca taaaggactg acaaaacctg   6480
gataaggaaa aacctttttt ttctatgaat ttttttgtt ttttagggga aagggattct   6540
aagaatgtca tttaatgtac tttgcatcat gtctctagaa atatctttgt ccatagtggt   6600
ggtggagtct ctctctctct ctctcttttt gtttgcttct gttttctttc ttgtcttcat   6660
tctttctttt ctttttattt tctggtagca ggcctccata gaacaaatct aaaacacaac   6720
caccatagta atgtaaggag agcttcagtg gcacctcaaa acccaccctt cgagatctgt   6780
ccaaagacag tctcagaaag ctgcactgcc caccggctca gctttcattc aaaaaggctt   6840
ccaaggccaa ttctgtcttg aagtcaatgc atgtatttac tgtttgacag taaacccgct   6900
ctgccttctc cacgtccaag gctgtgcatt cgtctaatta gcgtcgtgta tgttttcctt   6960
ttattttttc caataaaaaa gcagtgggat gaaaattgct ttgatatata gcaggtaaca   7020
ttgaagctat tccatagcac ttaactgtag tgaatactgt gtcaccaatt ttgaaatcaa   7080
tttaatgttt aatgcaaatc cattacatgg tgctattata ggctgacaaa atgatttaca   7140
caaatgtgac aacttgggct caattcactc tgctttccaa cagtgtaaat gcatagcagt   7200
gtttatctgc atgagaacta tgcactaatc tatctgaaga aaaaaactat atcaactttg   7260
gtatctactt tccgtttact tcaatccttg cctttttggt cattgttata atgccagctt   7320
taggacagaa agaattataa gaaaaccagc ataatacctg atatattaaa atgtagtgcc   7380
```

-continued

```
tgtgaaatct gtattatatt gctcttctga agtaagattt ttctacaccg gtagccttcg   7440
ctgtctgtca gtcaggacct tctggtatag gtgatgtaaa ataaccgtac aatattaatg   7500
catgcgattc cataatgctt agtgaactgt atgaatatta ctcaaagtta tgttagtctt   7560
tttttccgac ttggttcttg tcagctaggt ttaaaggtat ttcactgaga acgcaaattc   7620
tgtcttttct tgatttcggc tgttttcagt attttggagg tatacattta cttaaattca   7680
gtattactcg tgttttgttt ttgtttttgt tttttgtttt ctttttccta ggggacaagc   7740
atgggtgttt gatttcagaa atcagtacct ggcgagattt ttgtctcaaa acgactattt   7800
gaatttcaag aactgtgctg cgaagacact ctgagaacat ttgcaagtca ggggcatttt   7860
ccttgaccct tgactgatgc tatgcggaga ctgatacatt ttcttaatgg acaatgttca   7920
agccaggtac ccatgcttga tctgtcttca caccagacct cctcatatta aaaggaaaaa   7980
taagaaaaaa aatgtaagaa atcacatggc tatttagttt catgcacagt tgcaatattt   8040
tcttcaaaaa taaaactctg tacaaacttt gggcccgatt cataagaaaa agaagtttgc   8100
tattaacacg ggattttttt aatatacttt ttttggtcta aatttgaaat tacttgcttc   8160
ccaaattaaa taaatttcat ctcatttttt tccctaaacc agcacccatc tgccttttat   8220
tccccaaaga gttacctttc ccagattagg gggatggtat gtggggagca gatagcggaa   8280
atgcttagaa agataagggg gaccacccac agctggtcgt gagaacaggg agacagtgtg   8340
tgggggtggg acctcatctg tgtgcctggt atcctgagtt ttacatgtag atgcattcgc   8400
ctatttgatt cagaaaaata aactttccca aaatgtgtct gaaccacaag agcatacagt   8460
ggaagtgcta cctctaatct aaccagagca ccttcatggt ggaagacacc caccaggtca   8520
tacaatgtga acttttgtat ctctgcagtg gtttcaagga caaatagtgt ccaatgtatt   8580
gggccatttt tcctgctgtt tttatactca acttctcaaa atgaaaaaag cttttatttt   8640
tcctttgact tatttgtgtt gttcttattt tttaaatttt tattttttga taatagtctg   8700
taagttagcc tttttgggtt tttttttttt ttttttggct tttttttttg tttgtttttt   8760
tttcttttga cattgcaacc gaaggtcata aggccgctag ctccgctggg acagaggctt   8820
gagagaacta acggctcggt gccttctccc tggtctcaga ccatcgtctc tgcactgcga   8880
aggcatttgg tagcctcgcc actgagatac taactagacc tagactagga gctttatcag   8940
gttctaggag gtcctttagg aagactctca aaggcaaatc cctgatcccc cgccccaccc   9000
ttagccctgc cctctcacca gagcaaaatt cactggggac ttttcccacc acacatggaa   9060
atctgtccac tcggaatacc tctgttttcc atttcaaatt gtagggggag gggatggaac   9120
acttccagtg atggtaagag atctgttatg aaacgaaaca ccccccgtgt taataacttg   9180
gtctgaaatc tgtttttatg agccgggccc cctgtgcctc tagtatactt gtattgactc   9240
tcatagttac ccttttagtt ttactgtgtt ctgtgaaaat ttgtaattgg ttgagaatca   9300
ctgtgggcgt ccattcttat tcaactaaat ctccacaggt tttttgagct ggtgtggatt   9360
agtttaactc ttgtattcaa ccattagtgc taccaccttc tcacattaca atacaattac   9420
tggaagcaag tactgcattt cctatgcaac aaaaaaggaa aaataaaaaa ttgctaatgc   9480
taaaaaaaaa aaaaaaaaa                                                 9499
```

NFIA IN GLIAL FATE DETERMINATION, GLIOMA THERAPY AND ASTROCYTOMA TREATMENT

CROSS-REFERENCE TO RELATED APPLICATIONS

The present application claims priority to U.S. Provisional Application Ser. No. 60/994,753, filed on Sep. 21, 2007, by Anderson et al. and entitled "NFIA IN GLIAL FATE DETERMINATION, GLIOMA THERAPY AND ASTROCYTOMA TREATMENT WITH RNAi," which is hereby expressly incorporated by reference in its entirety.

STATEMENT REGARDING FEDERALLY SPONSORED R&D

This invention was made with Government support under Grant No. RO1-NS23476, awarded by the National Institutes of Health. The Government has certain rights in this invention.

PARTIES OF JOINT RESEARCH AGREEMENT

This invention was made as a result of activities undertaken within the scope of a joint research agreement between the California Institute of Technology and Children's Hospital, Los Angeles.

SEQUENCE LISTING

The present application is being filed along with a sequence listing in electronic format. The sequence listing is provided as a file entitled CALTE044A.txt, created Sep. 19, 2008, which is 23.0 KB in size. The information in the electronic format of the sequence listing is incorporated herein by reference in its entirety.

FIELD OF THE INVENTION

Embodiments disclosed herein relate to molecular medicine, and in particular to compositions and methods that can be used for glioma and astrocytoma therapy and treatment.

DESCRIPTION OF THE RELATED ART

Gliomas, tumors derived from glia cells of the central nervous system (CNS) account for approximately 30% of all primary brain tumors in adults. The median survival rate is about 12 months. Gliomas are usually treated by surgery, chemotherapy, radiotherapy and/or fractionated stereotype radio surgery.

Gliomas are heterogeneous in their cellular content and can be divided into groups of astrocytomas, anablastic astrocytomas and glioblastoma multiformes. Traditional approaches to therapeutic intervention have relied upon either surgery, chemotherapy, or radiotherapy. Recent advances in molecular genetics have revealed many genetic mutations and associated signaling pathways that may play a causative role in the generation of gliomas. While these advances have provided numerous candidate pathways that can be utilized in the development of rational therapy rooted in the biology of the disease, it remains to be seen whether such approaches will come to fruition. As such, there is a continued need for gliomal therapies.

The Nuclear Factor I (NFI) family of genes are glial fate determinants in the developing central nervous system. Interestingly, NFIA is also expressed in all grades of human astroctyoma, the most deadly form of glioma. Described herein is Applicants' discovery that NFIA plays a causative role in glioma formation and Applicants' discovery of therapeutics based on the elucidation of NFIA's role in glioma formation.

SUMMARY OF THE INVENTION

Provided herein are methods and compositions for glioma therapy and treatment. Some embodiments provided herein relate to methods for reducing the size of a glioma. Some embodiments relate to methods of arresting or slowing the development or progression of gliomal tumors. In some embodiments, the gliomas can be astrocytomas.

In some embodiments, the methods described herein include the steps of contacting a glioma with a therapeutically effective amount of an NFIA inhibitor. In some embodiments, the NFIA inhibitor can include an NFIA antisense polynucleotide, such as an NFIA short hairpin RNA (shRNA). In some embodiments, the shRNA NFIA inhibitor can target human NFIA. For example, in some embodiments, the NFIA inhibitor can be an NFIA shRNA that comprises the sequence of SEQ ID NO: 1. In some embodiments, the contacting step comprises contacting the glioma with a viral expression vector that encodes an NFIA antisense polynucleotide, such as a lentiviral expression vector.

In some embodiments, the NFIA inhibitor can be an antibody that specifically binds to NFIA.

Some embodiments provide an NFIA antisense polynucleotide. In some embodiments, the NFIA antisense polynucleotide comprises an isolated polynucleotide comprising the sequence of SEQ ID NO: 1.

BRIEF DESCRIPTION OF THE DRAWINGS

FIG. 4A-4D are images of MRIs of genetically modified U87 cells implanted into a mouse brain, 28 days post implantation. The arrows denote tumor growth.

DETAILED DESCRIPTION OF THE PREFERRED EMBODIMENT

Figure 1:
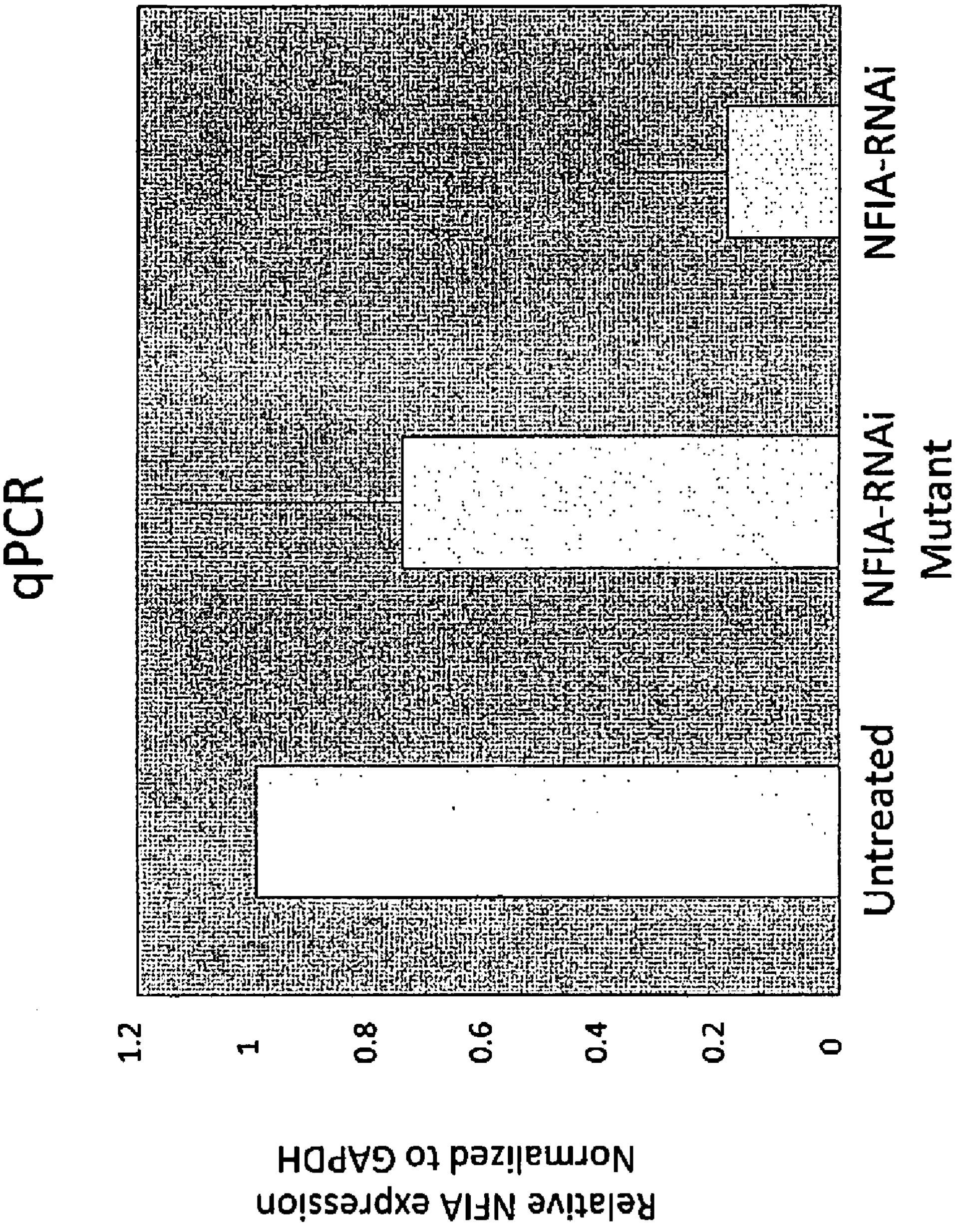
FIG. 1 is a bar graph showing the relative expression levels of NFIA in U87 glioma cells that were either untreated, treated with a mutant NFIA shRNA, or treated with an NFIA shRNA that targets human NFIA.

The embodiments disclosed herein relate to the treatment of gliomas and are based, in part, on Applicants' discovery that Nuclear Factor IA (NFIA) plays a role in glioma formation.

Embodiments herein relate to methods for treating gliomas, for reducing the tumor size of gliomas, and for reducing the functional NFIA levels in gliomas with NFIA inhibitors. The term "NFIA inhibitor" refers to a compound or composition that reduces the functional NFIA levels in a target cell (e.g., a glioma cell). NFIA inhibitors can function by inhibiting the expression of NFIA, for example by inhibiting transcription, translation, or processing of NFIA, or by inhibiting a functional activity of NFIA, such as DNA binding. NFIA inhibitors include, but are not limited to, antisense polynucleotides, antibodies, and small molecule inhibitors of NFIA.

NFIA Antisense Polynucleotides

In some embodiments, an NFIA inhibitor can be an NFIA antisense polynucleotide. Examples of antisense polynucleotides useful in the embodiments disclosed herein include single-stranded DNAs and RNAs that bind to complementary target mRNA and inhibit translation and/or induce RNaseH-mediated degradation of the target transcript; siRNA oligonucleotides, which are short, double-stranded RNAs that activate the RNA interference (RNAi) pathway leading to target mRNA degradation; ribozymes, which are oligonucleotide-based endonucleases that are designed to cleave specific mRNA transcripts; and nucleic acid aptamers and decoys, which are non-naturally occurring oligonucleotides that bind to and block protein targets in a manner analogous to small molecule drugs.

As used herein, the term "oligonucleotide" refers to an oligomer or polymer of nucleic acids such as ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Modified or substituted oligonucleotides provide desirable properties such as, for example, enhanced cellular uptake, enhanced affinity for nucleic acid target and increased stability in the presence of nucleases.

In addition to antisense oligonucleotides that comprise only naturally occurring nucleobases, in some embodiments, the antisense oligonucleotides provided herein can be oligomeric oligonucleotide mimetics. Accordingly, in some embodiments, antisense compounds provided herein include oligonucleotides containing modified backbones or non-natural internucleoside linkages. Oligonucleotides having modified backbones include those that retain a phosphorus atom in the backbone and those that do not have a phosphorus atom in the backbone.

In some embodiments, the antisense polynucleotides comprise oligomeric oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 21 to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference in its entirety.

In some embodiments, NFIA antisense polynucleotides can comprise modified oligonucleotide backbones that do not include a phosphorus atom. NFIA antisense polynucleotides can have backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In some embodiments, NFIA antisense polynucleotides can comprise mimetics wherein both the sugar and the internucleoside linkage, i.e., the backbone, of the nucleotide units are replaced with non-naturally occurring groups. In some embodiments, the base units are maintained for hybridization with an appropriate target polynucleotides. For example, some embodiments provide NFIA antisense polynucleotides that comprise a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497-1500.

In some embodiments, NFIA antisense oligonucleotides can have phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(C_{H3})—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Other mimetics that are present in some embodiments of the antisense polynucleotides disclosed herein include morpholino backbone structures described in U.S. Pat. No. 5,034,506, herein incorporated by reference in its entirety.

In some embodiments, the NFIA antisense polynucleotides can contain one or more substituted sugar moieties. In some embodiments, the antisense oligonucleotides disclosed herein comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In some embodiments, the antisense oligonucleotides can include one of the following groups at the 2' position: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_n CH_3)]_2$, where n and m are from 1 to about 10. In some embodiments, the antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some embodiments, the antisense oligonucleotides include 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. In some embodiments, the antisense polynucleotides or oligonucleotides disclosed herein include 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

In some embodiments, the NFIA antisense polynucleotides and oligonucleotides can include Locked Nucleic Acids (LNAs) in which the 2'-hydroxyl group is linked to the 3' or 4' carbon atom of the sugar ring thereby forming a bicyclic sugar moiety. The linkage can be a methelyne $(—CH_2—)_n$ group bridging the 2' oxygen atom and the 4' carbon atom wherein n is 1 or 2. LNAs and preparation thereof are described in WO 98/39352 and WO 99/14226, each of which is herein incorporated by reference in its entirety.

In some embodiments, the NFIA antisense polynucleotides and oligonucleotides can include 2'-methoxy (2'-O—$CH_3$), 2'-aminopropoxy (2'-$OCH_2CH_2CH_2NH_2$), 2'-allyl (2'-$CH_2$—CH.dbd.$CH_2$), 2'-O-allyl (2'-O—$CH_2$—CH.dbd.$CH_2$—) and 2'-fluoro (2'-F). The 2'-modification may be in the arabino (up) position or ribo (down) position. In some embodiments, the 2'-arabino modification is 2'-F. Similar modifications may also be made at other positions on the oligonucleotide, particularly the 3' position of the sugar on the 3' terminal nucleotide or in 2'-5 linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference, and U.S. Pat. No. 5,750,692, which is commonly owned with the instant application and also herein incorporated by reference.

In some embodiments, the NFIA antisense oligonucleotides can be chemically linked to one or more moieties or conjugates which enhance the activity, cellular distribution or cellular uptake of the oligonucleotide. For example, in some embodiments, the NFIA antisense oligonucleotides can include conjugate groups covalently bound to functional groups such as primary or secondary hydroxyl groups. Exemplary conjugate groups include intercalators, reporter molecules, polyamines, polyamides, polyethylene glycols, polyethers, groups that enhance the pharmacodynamic properties of oligomers, and groups that enhance the pharmacokinetic properties of oligomers, and groups that reduce the anionic charge of the polynucleotides, thereby enhancing transport across cellular membranes. Conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of the NFIA antisense oligonucleotides disclosed herein, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed for example in International Patent Application PCT/US92/09196, filed Oct. 23, 1992, and PCT/US2007/003641, filed Feb. 9, 2007, the entire disclosures of which are incorporated herein by reference in their entireties.

Other exemplary conjugate moieties useful in the embodiments disclosed herein include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic, for example. Oligonucleotide-drug conjugates and their preparation are described for example in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

In some embodiments, some or all positions in an NFIA antisense oligonucleotide or polynucleotide can be modified. In other embodiments, the NFIA antisense oligonucleotides do not contain any modified units. In still other embodiments, the NFIA antisense oligonucleotides disclosed herein are not uniformly modified. In some embodiments, more than one of the aforementioned modifications can be incorporated in a single NFIA antisense polynucleotide or oligonucleotide, or even at a single nucleoside within an oligonucleotide.

In some embodiments, the antisense compounds are chimeric. As used herein, the term "chimeric" antisense compounds or "chimeras," refer to antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

In some embodiments, chimeric NFIA antisense compounds can be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

NFIA antisense compounds disclosed herein can be conveniently and routinely made through the well-known technique of solid phase synthesis. Equipment for such synthesis is sold by several vendors including, for example, Applied Biosystems (Foster City, Calif.), BioAutomation (Irving, Tex.), or the like. Any other means for such synthesis known in the art may additionally or alternatively be employed. It is well known to use similar techniques to prepare oligonucleotides such as the phosphorothioates and alkylated derivatives.

NFIA antisense polynucleotides and oligonucleotides provided herein include any pharmaceutically acceptable salts, esters, or salts of such esters, or any other compound which, upon administration to an animal including a human, is capable of providing (directly or indirectly) the biologically active metabolite or residue thereof. Accordingly, for example, NFIA antisense polynucleotides and oligonucleotides can include prodrugs and pharmaceutically acceptable salts of the antisense polynucleotides, pharmaceutically acceptable salts of such prodrugs, and other bioequivalents.

As used herein, the term "prodrug" indicates a therapeutic agent that is prepared in an inactive form that is converted to an active form within the body or cells thereof by the action of endogenous enzymes or other chemicals and/or conditions. By way of example only, some embodiments provide prodrug versions of the NFIA antisense polynucleotides and oligonucleotides prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

In some embodiments, the NFIA antisense polynucleotides can be 5-10-mers, 10-15-mers, 15-20 mers, 20-25 mers, 25-30-mers, 30-40-mers, 40-45-mers, 45-50-mers, 50-55-mers, 55-60-mers, 60-65-mers, 65-70-mers, 70-75-mers, 75-80-mers, 80-85-mers, 85-90-mers, 90-95-mers, 95-100-mers, 100-120-mers, 120-140-mers, 140-160-mers, 160-180-mers, 180-200-mers, or greater, or any number in between, including full length genes or RNA transcripts thereof. In some embodiments the NFIA antisense polynucleotide can be, for example, a 43-55-mer that forms a hairpin, wherein about 4-5 of the nucleotide/modified subunits form the turn.

In some embodiments, NFIA antisense polynucleotides target human NFIA. Several sequences of human NFIA are publicly available, and can be found, for example, under GENBANK™ accession numbers NM 005595 (SEQ ID NO: 3); NM 001134673 (SEQ ID NO: 4). In some embodiments, NFIA antisense polynucleotides target NFIA from a different organism, such as a different mammal, such of mice, rats, rabbits, guinea pigs, dogs, cats, sheep, goats, cows, primates, such as monkeys, chimpanzees, and apes, and the like. The skilled artisan will readily appreciate, however, that antisense NFIA polynucleotides can be designed to target any NFIA sequence now known or discovered in the future Accordingly, some embodiments provide NFIA antisense polynucleotides that comprise NFIA shRNA sequences. Exemplary NFIA shRNA antisense polynucleotides include, but are not limited to, polynucleotides that comprise, consist essentially of, or consist of at least about 20 consecutive nucleic acids of the nucleic acid sequence of SEQ ID NO: 1, or mimetics thereof. In some embodiments, the NFIA shRNA can have at least 80%, 81%, 82%, 83%, 84%, 85%, 86%, 87%, 88%, 89%, 90%, 91%, 91%, 92%, 93%, 94%, 95%, 96%, 97%, 98%, 99%, or more sequence identity to at least 20 nucleotides of the nucleic acid sequence of SEQ ID NO: 1. Sequence identity can be determined using mathematical algorithms known to those skilled in the art. A non-limiting example of a mathematical algorithm utilized for comparison of sequences is the algorithm of Karlin S and Altschul S F, Proc. Natl. Acad. Sci. USA 87:2264-68 (1990), modified as in Karlin S and Altschul S F, Proc. Natl. Acad. Sci. USA 90:5873-77 (1993). Such an algorithm is incorporated into the NBLAST and XBLAST programs (version 2.0) of Altschul S F et al., J. Mol. Biol. 215:403-10 (1990). BLAST nucleotide searches can be performed with the NBLAST program score=100, wordlength=12 to obtain homologous nucleotide sequences. Another non-limiting algorithm useful for the comparison of sequences is the algorithm of Myers E W and Miller W, Comput. Appl. Biosci. 4:11-17 (1988). Such an algorithm is incorporated into the ALIGN program (version 2.0) which is part of the GCG sequence alignment software package. Another example of a mathematical algorithm utilized for the alignment of nucleic acid sequences is the Wilbur-Lipman algorithm (Wilbur W J and Lipman D J, Proc. Natl. Acad. Sci. USA 80:726-30 (1983)). When using the Wilbur-Lipman algorithm, a window of 20, gap penalty of 3, Ktuple of 3 can be used. Both The Wilbur-Lipman algorithm is incorporated, for example, into the MEGALIGN program (e.g., version 3.1.7) which is part of the DNASTAR sequence analysis software package.

Additional algorithms for sequence analysis are known in the art, and include ADVANCE and ADAM, described in Torelli A and Robotti C A, Comput. Appl. Biosci. 10:3-5 (1994); and FASTA, described in Pearson W R and Lipman D J, Proc. Natl. Acad. Sci. USA 85:2444-48 (1988).

In addition to the sequences set forth above, the skilled artisan will appreciate that various other regions of the NFIA coding sequence can be used as siRNA antisense targets, and are useful in the methods described herein. Antisense targets are generally 15-25 bases long, and refer to the region of an mRNA to which an antisense compound hybridizes. Determination of regions of the NFIA coding sequence useful as NFIA inhibitors is NFIA siRNA antisense targets can be selected using routine methods known to those skilled in the art. For example, siRNA targets are routinely identified by scanning an mRNA sequence for AA dinucleotides and recording the 19 nucleotides immediately downstream of the AA. Other methods can also been used to select the siRNA targets. In one example, the selection of the siRNA target sequence is purely empirically determined (see, e.g., Sui G et al., Proc. Natl. Acad. Sci. USA 99:5515-20 (2002)), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (see, e.g., Lee N S et al., Nature Biotechnol. 20:500-05 (2002)).

In another embodiment, an NFIA antisense hairpin siRNA expression cassette is constructed to contain the sequence corresponding to the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

In some embodiments, the length of nucleotide sequences that serve as each side of the stem of the hairpin siRNA expression cassette can range, for instance, from 19 to 29 or more. In some embodiments, the loop size can range from 3 to 23 nucleotides. The skilled artisan will appreciate that other lengths and/or loop sizes suitable for siRNAs can also be used. For example, in some embodiments, the stem of the hairpin can be greater than 29 bases long, e.g., 30-50, bases, or more. In some embodiments, the stem of the hairpin can be less than 29 bases, e.g. 5-28 bases. In some embodiments, the loop can be greater than 23 bases long, e.g., 24-50 bases.

In yet another embodiment, a 5' overhang in the hairpin siRNA construct can be used, provided that the hairpin siRNA provides the described therapeutic benefit, or reduces the levels of functional NFIA as described herein. In one specific example, the 5' overhang includes about 6 nucleotide residues.

In still yet another embodiment, the target sequence for RNAi is a 21-mer sequence. The 5' end of the target sequence has the dinucleotide "NA", where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a row.

Additional criteria can also be used for selecting RNAi target sequences. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases may be excluded. Furthermore, the remaining 19-mer sequence can be selected to have low sequence homology to other genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected.

The effectiveness of the siRNA sequences, as well as any other RNAi sequence according to the embodiments disclosed herein, can be evaluated using various methods known in the art. For instance, an NFIA siRNA sequence of the present invention can be introduced into a cell that expresses the NFIA gene. The polypeptide or mRNA level of the NFIA gene in the cell can be detected. A substantial change in the expression level of the NFIA gene before and after the introduction of the siRNA sequence is indicative of the effectiveness of the siRNA sequence in suppressing the expression of the NFIA gene. In one specific example, the expression levels of other genes are also monitored before and after the introduction of the siRNA sequence. An siRNA sequence which has inhibitory effect on NFIA gene expression but does not significantly affect the expression of other genes can be selected. In another specific example, multiple siRNA or other RNAi sequences can be introduced into the same target cell. These siRNA or RNAi sequences specifically inhibit NFIA gene expression but not the expression of other genes. In yet another specific example, siRNA or other RNAi sequences that inhibit the expression of the NFIA gene and one or more additional genes can be used.

Anti-NFIA Antibodies

In some embodiments, an NFIA inhibitor can be an anti-NFIA antibody. The term "antibody" is used in the broadest sense and specifically covers, for example, single anti-NFIA monoclonal antibodies (e.g. antagonist, and neutralizing antibodies), anti-NFIA antibody compositions with polyepitopic specificity, single chain anti-NFIA antibodies, and fragments of anti-NFIA antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts. NFIA antibodies useful in the embodiments described herein are commercially available, or can be generated using routine methods known to those skilled in the art.

Routine screening can be used to identify anti-NFIA-antibodies that are useful in the methods described herein, e.g., to reduce the activity of NFIA, to reduce tumor size, to treat gliomas, etc. Such screening methods include those detailed in the examples herein.

Polyclonal anti-NFIA antibodies can be prepared as described above by immunizing a suitable subject with an NFIA immunogen. The anti-NFIA antibody titer in the immunized subject can be monitored over time by standard techniques, such as with an enzyme linked immunosorbent assay (ELISA) using immobilized NFIA polypeptide. If desired, the antibody molecules directed against a NFIA polypeptide can be isolated from the mammal (e.g., from the blood) and further purified by well known techniques, such as protein A chromatography to obtain the IgG fraction. At an appropriate time after immunization, for example, when the anti-NFIA antibody titers are highest, antibody-producing cells can be obtained from the subject and used to prepare monoclonal antibodies by standard techniques, such as the hybridoma technique originally described by Kohler G and Milstein C, Nature 256:495-97 (1975) (see also, Brown J P et al., J. Immunol. 127:539-46 (1981); Brown J P et al., J. Biol. Chem. 255:4980-83 (1980); Yeh M Y et al., Proc. Natl. Acad. Sci. USA 76:2927-31 (1979); Yeh M Y et al., Int. J. Cancer 29:269-75 (1982)), the more recent human B cell hybridoma technique (Kozbor D and Roder J C, Immunol. Today 4:72-79 (1983)), the EBV-hybridoma technique (Cole et al. (1985), Monoclonal Antibodies and Cancer Therapy, Alan R. Liss, Inc., pp. 77-96), or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); Lerner E A, Yale J. Biol. Med., 54:387-402 (1981); Gefter M L et al., Somatic Cell Genet. 3:231-36 (1977)). Briefly, an immortal cell line (typically a myeloma) is fused to lymphocytes (typically splenocytes) from a mammal immunized with a Ccdc80 immunogen as described above, and the culture supernatants of the resulting hybridoma cells are screened to identify a hybridoma producing a monoclonal antibody that binds specifically to a Ccdc80 polypeptide Any of the many well known protocols used for fusing lymphocytes and immortalized cell lines can be applied for the purpose of generating an anti-NFIA monoclonal antibody (see, e.g., Galfre G et al., Nature 266:550-52 (1977); Geifer M L et al., supra; Lerner E A, supra; Kenneth, Monoclonal Antibodies, supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, for example, the P3-NS1/1-Ag4-1, P3-x63-Ag8.653 or Sp2/0-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a NFIA molecule, for example, using a standard ELISA assay.

As an alternative to preparing monoclonal antibody-secreting hybridomas, a monoclonal anti-NFIA antibody can be identified and isolated by screening a recombinant combinatorial immunoglobulin library (e.g., an antibody phage display library) with NFIA to thereby isolate immunoglobulin library members that bind a NFIA polypeptide. Kits for generating and screening phage display libraries are commercially available (e.g., the GE Healthcare Recombinant Phage Antibody System, Catalog No. 27-9400-01). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs P et al., Biotechnology (N.Y.) 9:1370-72 (1991); Hay B N et al., Hum. Antibodies Hybridomas 3:81-85 (1992); Huse W D et al., Science 246:1275-81 (1989); Griffiths A D et al., EMBO J. 12:725-34 (1993); Hawkins R E et al., J. Mol. Biol. 226:889-96 (1992); Clarkson T et al., Nature 352:624-28 (1991); Gram H et al., Proc. Natl. Acad. Sci. USA 89:3576-80 (1992); Garrard L J et al., Biotechnology (N.Y.) 9:1373-77 (1991); Hoogenboom H R et al., Nucleic Acids Res. 19:4133-37 (1991); Barbas C F et al., Proc. Natl. Acad. Sci. USA 88:7978-82 (1991); and McCafferty J et al., Nature 348:552-54 (1990).

Additionally, recombinant anti-NFIA antibodies, such as chimeric and humanized monoclonal antibodies, comprising both human and non-human portions, can be produced by recombinant DNA techniques known in the art, for example using methods described in WO 87/02671; EP 0 184 187; EP 0 171 496; EP 0 173 494; WO 86/01533; U.S. Pat. No. 4,816,567; EP 0 125 023; Better M et al., Science 240:1041-43 (1988); Liu A Y et al., Proc. Natl. Acad. Sci. USA 84:3439-43 (1987); Liu A Y et al., J. Immunol. 139:3521-26 (1987); Sun L K et al., Proc. Natl. Acad. Sci. USA 84:214-18 (1987); Nishimura Y et al., Cancer Res. 47:999-1005 (1987); Wood C R et al., Nature 314:446-49 (1985); Shaw D R et al., J. Natl. Cancer Inst. 80:1553-59 (1988); Morrison S L, Science 229: 1202-07 (1985); U.S. Pat. No. 5,225,539; Verhocyan M et al., Science 239:1534-36 (1988); and Beidler C B et al., J. Immunol. 141:4053-60 (1988).

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable genetic display package and vectors containing nucleic acid molecules encoding a second polypeptide chain of a single binding pair member using techniques known in the art, for example, as described in U.S. Pat. No. 5,565,332; 5,871,907; or 5,733,743.

In some embodiments, anti-NFIA antibodies that recognize intracellular NFIA can be used, e.g., intracellularly to inhibit NFIA protein activity. The use of intracellular antibodies to inhibit protein function in a cell is known in the art (see e.g., Carlson J R, Mol. Cell. Biol. 8:2638-46 (1988); Biocca S et al., EMBO J. 9:101-08 (1990); Werge T M et al., FEBS Lett. 274:193-98 (1990); Carlson J R, Proc. Natl. Acad. Sci. USA 90:7427-28 (1993); Marasco W A et al., Proc. Natl. Acad. Sci. USA 90:7889-93 (1993); Biocca S et al., Biotechnology (N.Y.) 12:396-99 (1994); Chen S-Y et al., Hum. Gene Ther. 5:595-601 (1994); Duan L et al., Proc. Natl. Acad. Sci. USA 91:5075-79 (1994); Chen S-Y et al., Proc. Natl. Acad. Sci. USA 91:5932-36 (1994); Beerli R R et al., J. Biol. Chem. 269:23931-36 (1994); Beerli R R et al., Biochem. Biophys. Res. Commun. 204:666-72 (1994); Mhashilkar A M et al., EMBO J. 14:1542-51 (1995); Richardson J H et al., Proc. Natl. Acad. Sci. USA 92:3137-41 (1995); WO 94/02610; and WO 95/03832).

In one embodiment, a recombinant expression vector is prepared which encodes the antibody chains in a form such that, upon introduction of the vector into a cell, the antibody chains are expressed by the cell as a functional antibody. For inhibition of NFIA activity according to the inhibitory methods of the invention, an intracellular antibody that specifically binds NFIA protein is preferably secreted from the cell.

To prepare an antibody expression vector, antibody light and heavy chain cDNAs encoding antibody chains specific for the target protein of interest, for example, Ccdc80, are isolated, typically from a hybridoma that secretes a monoclonal antibody specific for the NFIA protein. Hybridomas secreting anti-NFIA monoclonal antibodies, or recombinant anti-NFIA monoclonal antibodies, can be prepared as described above. Once a monoclonal antibody specific for NFIA protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat E A et al. (1991) Sequences of Proteins of Immunological Interest, Fifth Edition, U.S. Department of Health and Human Services, NIH Publication No. 91-3242 and in the "Vbase" human germline sequence database.

Once obtained, the antibody light and heavy chain sequences are cloned into a recombinant expression vector using standard methods. An antibody expression vector can encode an antibody in one of several different forms. For example, in one embodiment, the vector encodes full-length antibody light and heavy chains such that a full-length antibody is expressed. To inhibit NFIA activity in a cell, the expression vector encoding the anti-NFIA intracellular or extracellular antibody is introduced into the cell by standard transfection methods, as discussed herein.

Anti-NFIA antibodies that function as NFIA inhibitors can be identified by screening for a desired inhibitory activity, for example, by using the methods described in the examples and elsewhere in the disclosure. For example, anti-NFIA antibodies can be screened in vitro for their ability to slow or arrest growth of gliomas, to decrease NFIA expression in gliomal cells, inhibiot NFIA activity (e.g., inhibit transcription of NFIA-induced genes, etc), or the like.

Pharmaceutical Compositions and Methods

In some embodiments, the methods disclosed herein (e.g., reduction of NFIA activity, treatment of gliomas, treatment of astrocytomas, etc.) involve contacting a glioma with an effective amount of an NFIA inhibitor. The terms "effective amount", "therapeutically effective amount", and "effective dosage" as used herein refer to the amount of an NFIA inhibitor that is effective to at least slow the rate of glioma tumor growth, slow or arrest the progression of glioma, or decrease glioma tumor size. Tumor growth and tumor size can be measured using routine methods known to those skilled in the art, including, for example, magnetic resonance imagine and the like. Gliomas can be subdivided based on the WHO grading system into grade I-IV, with grade I reflecting a benign, highly differentiated tumor and grades II-IV marking increasing states of malignancy, and decreasing degrees of differentiation. In some embodiments, an "effective amount" of an NFIA inhibitor is an amount effective to result in a downgrading of a tumor, or an amount effective to slow or prevent the progression of a glioma to a higher grade.

In embodiments wherein the NFIA inhibitor is a antisense oligonucleotide, for example, a an "effective amount" can refer to the amount of NFIA inhibitor necessary to cause "knock-down" of NFIA expression relative to levels present following administration or expression of a non-targeting control RNA (e.g., a non-targeting control siRNA). Knock-down of expression of an amount including and between 50% and 100%, e.g., 55%, 60%, 65%, 70%, 75%, 80%, 85%, 90%, 95%, 97%, 98%, 99% or more, is contemplated by embodiments herein. Knock-down can be assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

In some embodiments, the methods disclosed herein include contacting a glioma or glioma target cell with an effective amount of an NFIA inhibitor. In embodiments wherein the NFIA inhibitor comprises a polynucleotide, (including recombinant expression vectors encoding NFIA antisense RNA, intracellular NFIA antibodies, or dominant negative NFIA inhibitors), the agents can be introduced into cells of the glioma using methods known in the art for introducing polynucleotides (e.g., DNA, RNA or the like) into cells in vivo. Examples of such methods encompass both non-viral and viral methods, including but not limited to the methods described below.

Direct Injection: Naked polynucleotides can be introduced into cells or glioma in vivo by directly injecting the polynucleotides into the cells or glioma (see, e.g., Acsadi G et al., Nature 332:815-18 (1991); Wolff J A et al., Science 247: 1465-68 (1990)). For example, a delivery apparatus (e.g., a "gene gun") for injecting polynucleotides into cells in vivo can be used. Such an apparatus is commercially available (e.g., from Bio-Rad Laboratories, Hercules, Calif.). In some embodiments, gliomas are contacted with NFIA inhibitors via direct injection of the NFIA inhibitor to the glioma.

Cationic Lipids: Naked polynucleotides can be introduced into cells in vivo by complexing the polynucleotides with cationic lipids or encapsulating the polynucleotides in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan J J et al., Gene Ther. 2:38-49 (1995); San H et al., Hum. Gene Ther. 4:781-88 (1993)).

Receptor-Mediated DNA Uptake: Naked polynucleotides can also be introduced into cells in vivo by complexing the polynucleotides to a cation, such as polylysine, which is coupled to a ligand for a cell-surface receptor (see, e.g., Wu G Y and Wu C H, J. Biol. Chem. 263:14621-24 (1988); Wilson J M et al., J. Biol. Chem. 267:963-67 (1992); and U.S. Pat. No. 5,166,320). Binding of the polynucleotide-ligand complex to the receptor facilitates uptake of the polynucleotide by receptor-mediated endocytosis. A polynucleotide-ligand complex linked to adenovirus capsids which naturally disrupt endosomes, thereby releasing material into the cytoplasm can be used to avoid degradation of the complex by intracellular lysosomes (see, e.g., Curiel D T et al., Proc. Natl. Acad. Sci. USA 88:8850-54 (1991); Cristiano R J et al., Proc. Natl. Acad. Sci. USA 90:2122-26 (1993)). In some embodiments, gliomas are contacted with NFIA inhibitors via receptor mediated uptake of the NFIA inhibitor.

Retroviruses: Modified retroviruses are well characterized for use in gene transfer for gene therapy purposes (for a review, see Miller A D, Blood 76:271-78 (1990)). A recombinant retrovirus can be constructed having a nucleotide sequence of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel F M et al. (eds.) Greene Publishing Associates, (1989), Sections 9.10-9.14 and other standard laboratory manuals. Examples of suitable retroviruses include pLJ, pZIP, pWE, and pEM which are well known to those skilled in the art. Examples of suitable packaging virus lines include ψpCrip, ψpCre, ψp2 and ψpAm. Retroviruses have been used to introduce a variety of genes into many different cell types, including epithelial cells, endothelial cells, lymphocytes, myoblasts, hepatocytes, bone marrow cells, in vitro and/or in vivo (see, e.g., Eglitis M A et al., Science 230:1395-98 (1985); Danos O and Mulligan R C, Proc. Natl. Acad. Sci. USA 85:6460-64 (1988); Wilson J M et al., Proc. Natl. Acad. Sci. USA 85:3014-18 (1988); Armentano D et al., Proc. Natl. Acad. Sci. USA 87:6141-45 (1990); Huber B E et al., Proc. Natl. Acad. Sci. USA 88:8039-43 (1991); Ferry N et al., Proc. Natl. Acad. Sci. USA 88:8377-81 (1991); Chowdhury J R et al., Science 254:1802-05 (1991); van Beusechem V W et al., Proc. Natl. Acad. Sci. USA 89:7640-44 (1992); Kay M A et al., Hum. Gene Ther. 3:641-47 (1992); Dai Y et al., Proc. Natl. Acad. Sci. USA 89:10892-95 (1992); Hwu P et al., J. Immunol. 150:4104-15 (1993); U.S. Pat. No. 4,868,116; U.S. Pat. No. 4,980,286; WO 89/07136; WO 89/02468; WO 89/05345; and WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell. In some embodiments, retroviruses are used to deliver NFIA inhibitors to gliomas.

Adenoviruses: The genome of an adenovirus can be manipulated such that it encodes and expresses a gene product of interest but is inactivated in terms of its ability to replicate in a normal lytic viral life cycle (see, e.g., Berkner K L, Biotechniques 6:616-29 (1988); Rosenfeld M A et al., Science 252:431-34 (1991); and Rosenfeld M A et al., Cell 68:143-55 (1992)). Suitable adenoviral vectors derived from the adenovirus strain Ad type 5 d1324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types, including airway epithelium (Rosenfeld M A et al., Cell 68:143-55 (1992)), endothelial cells (Lemarchand P et al., Proc. Natl. Acad. Sci. USA 89:6482-86 (1992)), hepatocytes (Herz J and Gerard R D, Proc. Natl. Acad. Sci. USA 90:2812-16 (1993)), and muscle cells (Quantin B et al., Proc. Natl. Acad. Sci. USA 89:2581-84 (1992)). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner K L et al., supra; Haj-Ahmad Y and Graham F L, J. Virol. 57:267-74 (1986)). Most replication-defective adenoviral vectors currently in use are deleted for all or parts of the viral E1 and E3 genes but retain as much as 80% of the adenoviral genetic material. In some embodiments, adenoviruses are used to deliver NFIA inhibitors to a glioma.

Adeno-Associated Viruses: Adeno-associated virus (AAV) is a naturally occurring defective virus that requires another virus, such as an adenovirus or a herpes virus, as a helper virus for efficient replication and a productive life cycle (for a review, see Muzyczka N, Curr. Top. Microbiol. Immunol. 158:97-129 (1992)). It is also one of the few viruses that may integrate its DNA into non-dividing cells, and exhibits a high frequency of stable integration (see, e.g., Flotte T R et al., Am. J. Respir. Cell. Mol. Biol. 7:349-56 (1992); Samulski R J et al., J. Virol. 63:3822-28 (1989); and McLaughlin S K et al., J. Virol. 62:1963-73 (1988)). Vectors containing as little as 300 base pairs of AAV can be packaged and can integrate. Space for exogenous DNA is limited to about 4.5 kb. An AAV vector such as that described in Tratschin J D et al., Mol. Cell. Biol. 5:3251-60 (1985), can be used to introduce the polynucleotides into cells. A variety of nucleic acids have been introduced into different cell types using AAV vectors (see, e.g., Hermonat P L and Muzyczka N, Proc. Natl. Acad. Sci. USA 81:6466-70 (1984); Tratschin J D et al., Mol. Cell. Biol. 4:2072-81 (1985); Wondisford F E et al., Mol. Endocrinol. 2:32-39 (1988); Tratschin J D et al., J. Virol. 51:611-19 (1984); and Flotte T R et al., J. Biol. Chem. 268:3781-90 (1993)). In some embodiments, adeno-associated viruses are used to deliver NFIA inhibitors to gliomas.

Lentiviruses: "Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. In some embodiments, the NFIA antisense oligonucleotides can be provided in an expression vector, such as a lentilviral vector. In some embodiments, an antisense NFIA polynucleotide (e.g., an NFIA shRNA oligonucleotide or the like), can be used to deliver the NFIA inhibitor to the glioma or target cell. In some embodiments, NFIA antisense compounds are provided in a modified lentivirus expression vector, such as those described in U.S. Pat. No. 7,195,916, herein incorporated by reference in its entirety.

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

Administration of NFIA Inhibitors

NFIA inhibitors can be administered to subjects in a biologically compatible form suitable for pharmaceutical administration in vivo to suppress NFIA activity. By "biologically compatible form suitable for administration in vivo" is meant a form of the NFIA inhibitor to be administered in which any toxic effects are outweighed by the therapeutic effects of the inhibitor. The term subject is intended to include living organisms in which an immune response can be elicited, for example, mammals. Administration of NFIA inhibitors as described herein can be in any pharmacological form including a therapeutically active amount of an agent alone or in combination with a pharmaceutically acceptable carrier.

Administration of a therapeutically active amount of the NFIA inhibitors disclosed herein is defined as an amount effective, at dosages and for periods of time necessary, to achieve the desired result. For example, a therapeutically active amount of a NFIA inhibitor may vary according to factors such as the disease state, age, sex, and weight of the individual, and the ability of peptide to elicit a desired response in the individual. Dosage regima may be adjusted to provide the optimum therapeutic response. For example, several divided doses may be administered daily, or the dose may be proportionally reduced as indicated by the exigencies of the therapeutic situation.

The therapeutic or pharmaceutical compositions of the present invention can be administered by any suitable route known in the art including, for example, intravenous, subcutaneous, intramuscular, transdermal, intrathecal, or intracerebral or administration to cells in ex vivo treatment protocols. Administration can be either rapid as by injection or over a period of time as by slow infusion or administration of slow release formulation.

NFIA inhibitors can be in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. NFIA inhibitors can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

In some embodiments, the NFIA inhibitors are formulated for oral administration. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents, or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

In some embodiments, NFIA inhibitors can be formulated for parenteral delivery. In some embodiments, parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the NFIA inhibitor and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of NFIA inhibitors can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. NFIA inhibitors which exhibit large therapeutic indices are preferred. While NFIA inhibitors that exhibit toxic side effects may be used, care should be taken to design a delivery system that targets such inhibitors to the gliomas in order to minimize potential damage to non-gliomal cells and, thereby, reduce side effects.

Data obtained from the cell culture assays and animal studies can be used in formulating a range of dosage for use in humans. The dosage of NFIA inhibitors lies preferably within a range of circulating concentrations that include the $ED_{50}$ with little or no toxicity. The dosage may vary within this range depending upon the dosage form employed and the route of administration utilized. For any NFIA inhibitor used in the methods described herein, the therapeutically effective dose can be estimated initially from cell culture assays.

The effectiveness of a NFIA inhibitor can be determined by a screening assay as described herein, such as determining the level of NIFA protein in gliomas, determining the tumor size of gliomas, or the like.

As such, some embodiments provide for the use of a NFIA inhibitor disclosed herein in the manufacture of a medicament for the reduction of glioma size, or for the treatment of glioma.

In some embodiments, a subject that has, or is at risk of developing a glioma is identified by routine diagnostic methods, e.g., with neurological exams to check vision, hearing balance, coordination, reflexes, and the like, imaging techniques such as MRI (with or without contrast enhancements), CT scans, and the like. In some embodiments, subjects identified as having, or at risk of developing, a glioma is administered a therapeutically effective amount of an NFIA inhibitor, as described herein. For example, in some embodiments, the subject's glioma is contacted with an NFIA inhibitor. In some embodiments, the size and progression of the subject's glioma is monitored before and after treatment with the NFIA inhibitor (e.g., with MRI, CT scans, or the like).

The following examples are presented in order to more fully illustrate some embodiments of the invention. They should, in no way be construed, however, as limiting the broad scope of the invention.

EXAMPLE 1

NFIA Small Hairpin RNA Reduces NFIA Expression in Glioma Cell Lines

This example describes the design of an exemplary NFIA shRNA.

To determine potential NFIA shRNA sequences, publicly available programs, including siRNA target designer, were used. The data generated by the designer programs was compared, and sequences that were identified by multiple programs were tested in vitro for silencing of cNFIA.

Briefly, the selected sequences were integrated into oligos containing a stem-loop sequence and engineered restriction enzyme sites to facilitate cloning. The format of the oligo design is as follows:

Forward 5' ACC - - - G(N20) - - - TTCAAGAGA - - - (20N)C - - - TTTTTA 3'

Reverse 3' - - - C(N20) - - - AAGTTCTCT - - - (20N) G - - - AAAAAAGCTT 5'

Oligonucleotides were synthesized using routine solid phase synthesis methods. The oligos were synthesized, annealed, kinase treated and cloned into a Bluescript-hU6 plasmid (a gift from D. Baltimore) (Qin et al. (2003) Proc. Nat. Acad. Sci. USA 100(1):183-188)) digested with Bbsl and HindIII. Clones were sequence verified, and the hU6-shRNAi cassette was shuttled into a lentiviral vector (FG-12/GFP (Qin et al., 2003).

The following NFIA antisense oligonucleotide sequence cNFIA resulted in complete knockdown of endogenous NFIA protein:

GAGGCACATGGAGAACTAAA (SEQ ID NO: 1).

As a control, a mutant NFIA antisense polynucleotide was generated, which has four base changes (underlined) compared to SEQ ID NO: 1, such that the antisense oligonucleotide would not anneal to and inhibit the endogenous NFIA transcript.

GATGCACGTGAAGACGTATA (SEQ ID NO: 2)

To generate the lentivirus, the lentiviral sh-RNAi DNA is co-transfected using routine methods into 293T cells along with DNA constructs that provide the necessary genetic components for efficient viral generation in trans. After transfection the supernatant is collected and concentrated. The resultant supernatant served as the viral substrate utilized in the experiments discussed below.

A second set of experiments, was performed to test whether the NFIA RNAi constructs described above efficiently reduced the level of NFIA expression in glioma cell lines. A small amount of the viral substrate described above was added to a plate of U87 human glioma cell lines. Efficient transduction of the lentivirus into the cells was measured by GFP expression. Forty-eight hours post infection, RNA was harvested from the cells and analyzed by quantitative PCR (qPCR).

U87 cells transfected with the NFIA-shRNAi described above exhibited an 80% reduction in the levels of NFIA transcript expression compared to untransfected U87 glioma cells (FIG. 1). By contrast, when the U87 cells were transfected with the NFIA-shRNAi mutant that contains five point mutations. In comparison with the mutant, the NFIA-RNAi demonstrated only a 75% reduction in transcript expression.

The data demonstrate that NFIA shRNA constructs can be used to reduce NFIA transcription in glioma cells.

The following example describes experiments to determine whether reduced levels of NFIA caused by NFIA-RNAi lead to an inhibition of growth in the U87 cell lines.

EXAMPLE 2

NFIA Small Hairpin RNA Reduces Growth of Glioma Cell Lines

To test the effects of NFIA antisense compositions on the growth of gliomas in vitro, the U87 cell line was transduced with the lentiviral NFIA-shRNAi viral supernatant, (described in Example 1) lentiviral NFIA-shRNAi-mutant viral supernatant (described in Example 1), or was left untreated.

Figure 2:
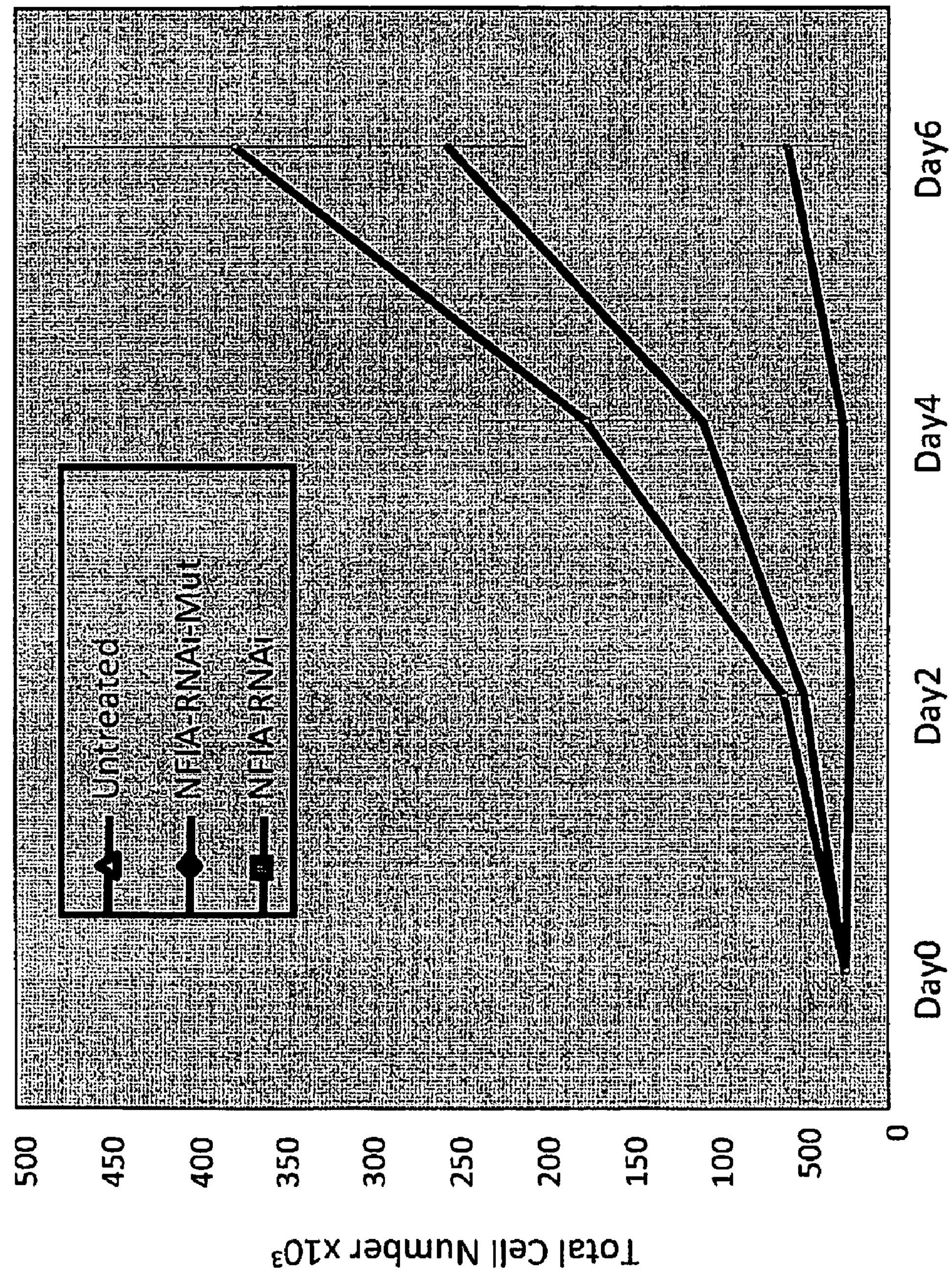
FIG. 2 is a graph showing the growth (as expressed in total cell number) of U87 glioma cells infected with either a viral construct encoding a human NFIA shRNA or a mutant version of the human NFIA shRNA, or that were not infected.

As shown in FIG. 2, transduction of gliomal cells with NFIA-shRNAi led to a dramatic reduction in cell growth compared to untreated U87 cells, and U87 cells transduced with the mutant-shRNAi lentivirus.

These data demonstrate that NFIA antisense inhibitors reduce growth of NFIA in gliomal cells, and demonstrate that NFIA antisense inhibitors are useful for the treatment of glioma.

The following example describes experiments to confirm whether NFIA plays an active role in tumorigenesis.

EXAMPLE 3

NFIA Small Hairpin RNA Reduces Gliomal Tumor Growth Rate In Vivo

To test whether NFIA antisense inhibitors reduce the growth of gliomal tumors, U87 gliomal cells were transduced with the lentiviral NFIA-shRNAi viral supernatant, lentiviral NFIA-shRNAi-mutant viral supernatant, or a lentilviral NFIA cDNA viral supernatant, as described in Example 1. Approximately $2.5\times10^5$ cells were injected intracranially into mice, and tumor formation and growth was monitored using MRI.

Figure 3:
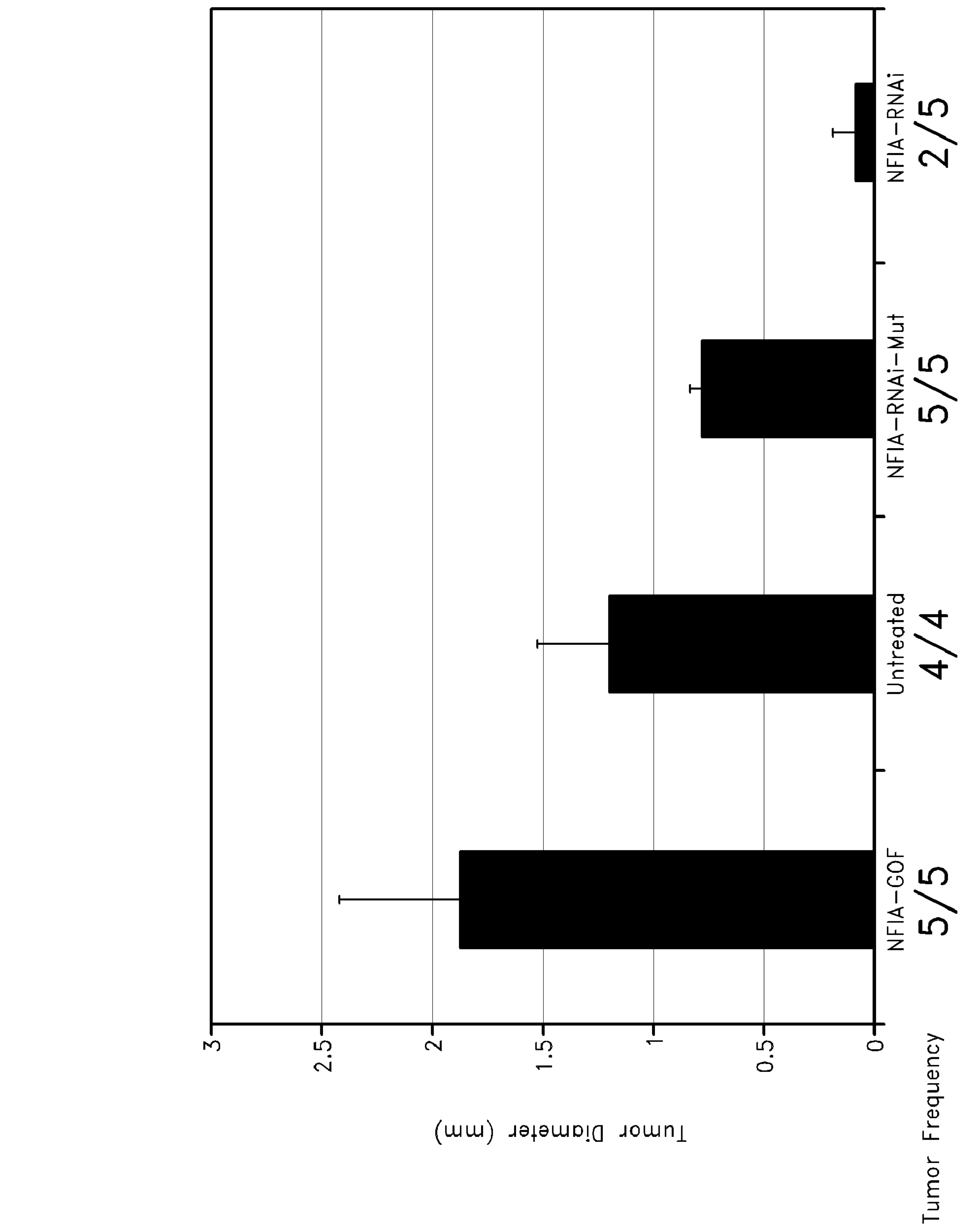
FIG. 3 is a graph showing the size and frequency of tumors in mice receiving transplants of: U87 glioma cells transduced with a lentiviral expression vector encoding NFIA cDNA; untreated U87 cells, U87 cells transduced with either a lentiviral construct encoding a NFIA shRNA; or U87 cells transduced with a lentiviral construct encoding a mutant version of the NFIA shRNA.

The results of the MRI are shown in FIGS. 3 and 4. As shown in FIG. 4A, over-expression of NFIA led to an accelerated rate of tumor growth, compared to tumor growth in mice injected with cells transduced with the lentiviral vector alone. FIG. 4B. By contrast, knockdown of NFIA expression in U87 cells with the shRNAi NFIA inhibitor led to a dramatic reduction in tumor size. FIG. 4D, FIG. 3. The reduction was not as pronounced in mice injected with U87 cells transduced with the mutant shRNAi NFIA lentiviral supernatant. FIG. 4C.

The data demonstrate that NFIA-RNAi NFIA inhibitor results in a dramatic reduction in the size and frequency of gliomal tumors.

The following example describes experiments to confirm that NFIA function is necessary for glioma formation, using a primary mouse neurosphere model of glioma.

EXAMPLE 4

Reduction of Gliomal Tumor Size in Primary Mouse Neurosphere Model of Glioma In order to determine whether NFIA function is necessary for glioma formation in a primary mouse neurosphere model, transgenic NFIA mice (described in Neves et al. Proc. Nat. Acad. Sci. USA (1999) 96(21):11946-11951) was used to generate NFIA+/− and NFIA−/− neurospheres from E11.5 telencephelon. Neurospheres were transduced with retroviruses expressing SV40 Large T antigen and constitutively activated EGFR-vIII. Expression of SV40 Large T antigen and EGFR-vIII were validated via immunocytochemistry (not shown). NFIA+/−; SV40:EGFR-vIII and NFIA-; SV40; EGFR-vIII neurospheres were injected subcutaneously into the necks of SCID mice. Six weeks post-injection, tumors were harvested and analyzed. The results are presented in Table 1.

TABLE 1

| Cell Line | Number of Mice with a 1.5 cm tumor at 6 weeks |
|---|---|
| NFIA +/−; SV40; EGFR-vIII | 5/5 |
| NFIA +/+; SV40; EGFR-vIII | 0/5 |

The data demonstrate that NFIA function is necessary for glioma formation in a primary mouse neurposphere model. As such, the data confirm that NFIA is a useful therapeutic target for glioma.

EXAMPLE 5

Reduction of Gliomal Tumor Size

This example illustrates the reduction of the size of a gliomal tumor in a subject.

A subject is identified as having, or at risk of developing a glioma such as an astrocytoma using routine diagnostic methods. The subject is administered a daily dose of an NFIA inhibitor, such that the NFIA inhibitor contacts the glioma (e.g., by injection of the NFIA inhibitor into the glioma). The daily dose of the NFIA inhibitor can, in some cases, range from about 0.01 μg/kg to about 1 mg/kg of subject body weight or more per day, depending on the factors mentioned above. Preferably the dose of the NFIA inhibitor ranges from about 10 μg/kg/day to about 100 μg/kg/day. The appropriate dosage and treatment regimen can be readily determined by the skilled artisan based on a number of factors, including but not limited to the nature of the NFIA inhibitor, and the subject's disease state (e.g., the size and/or stage of the glioma), or condition. Levels of NFIA within the glioma can be determined before and after administration of the NFIA inhibitor. The glioma tumor size can be determined before and after administration of the NFIA inhibitor.

EXAMPLE 6

Treatment of Astrocytoma

This example illustrates the treatment of an astrocytoma in a subject.

A subject is identified as having, or at risk of developing an astrocytoma using routine diagnostic methods. The subject is administered a daily dose of an NFIA inhibitor, such that the NFIA inhibitor contacts the astrocytoma (e.g., by injection of the NFIA inhibitor into the astrocytoma). The daily dose of the NFIA inhibitor can, in some cases, range from about 0.01 μg/kg to about 1 mg/kg of subject body weight or more per day, depending on the factors mentioned above. Preferably the dose of the NFIA inhibitor ranges from about 10 μg/kg/day to about 100 μg/kg/day. The appropriate dosage and treatment regimen can be readily determined by the skilled artisan based on a number of factors, including but not limited to the nature of the NFIA inhibitor, and the subject's disease state (e.g., the size and/or stage of the tumor), or condition. Levels of NFIA within the astrocytoma can be determined before and after administration of the NFIA inhibitor. The astrocytoma tumor size can be determined before and after administration of the NFIA inhibitor.

All patents and publications are herein incorporated by reference in their entireties to the same extent as if each individual publication was specifically and individually indicated to be incorporated by reference.

The invention illustratively described herein suitably can be practiced in the absence of nay element or elements, limitation or limitations that is not specifically disclosed herein. The terms and expression which have been employed are used as terms of description and not of limitation, and there is no intention that the use of such terms and expressions indicates the exclusion of equivalents of the features shown and described, or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

What is claimed is:

1. A method of reducing the size of an astrocytoma, comprising, contacting said astrocytoma with a therapeutically effective amount of an NFIA inhibitor, wherein said NFIA inhibitor is selected from the group consisting of an NFIA antisense polynucleotide and an anti-NFIA antibody.

2. The method of claim 1, wherein said NFIA inhibitor comprises an NFIA antisense polynucleotide.

3. The method of claim 2, wherein said NFIA inhibitor comprises an NFIA short hairpin RNA (shRNA).

4. The method of claim 3, wherein said shRNA targets human NFIA.

5. The method of claim 4, wherein the NFIA shRNA comprises the sequence of SEQ ID NO: 1.

6. The method of claim 2, wherein said contacting step comprises contacting said glioma with a viral expression vector that comprises said NFIA antisense polynucleotide.

7. The method of claim 1, wherein the contacting step comprises injecting said NFIA inhibitor into said astrocytoma.

8. The method of claim 1, wherein said NFIA inhibitor is an antibody that specifically binds to NFIA.

9. A method of treating an astrocytoma in a subject in need thereof, comprising identifying a subject with an astrocytoma; and contacting said astrocytoma with a therapeutically effective amount of an NFIA inhibitor, wherein said NFIA inhibitor is selected from the group consisting of an NFIA antisense polynucleotide and an anti-NFIA antibody.

10. The method of claim 9, wherein said NFIA inhibitor is an NFIA antisense polynucleotide.

11. The method of claim 10, wherein said NFIA antisense oligonucleotide comprises an NFIA short hairpin RNA (shRNA).

12. The method of claim 11, wherein the shRNA targets human NFIA.

13. The method of claim 12, wherein said shRNA comprises SEQ ID NO: 1.

14. The method of claim 10, wherein the NFIA inhibitor comprises a viral expression vector that comprises said NFIA antisense polynucleotide.

15. The method of claim 9, wherein the contacting step comprises injecting said NFIA inhibitor into said astrocytoma.

16. The method of claim 9, wherein said NFIA inhibitor is an antibody that specifically binds to NFIA.

17. A method of treating an astrocytoma, comprising reducing the amount of functional NFIA in the cells comprising said astrocytoma, wherein said reducing step comprises contacting said astrocytoma with an NFIA inhibitor, wherein said NFIA inhibitor is selected from the group consisting of an NFIA antisense polynucleotide and an anti-NFIA antibody.

18. The method of claim 17, wherein said NFIA inhibitor is an NFIA antisense polynucleotide.

19. The method of claim 18, wherein said NFIA antisense oligonucleotide comprises an NFIA short hairpin RNA (shRNA).

20. The method of claim 19, wherein the shRNA targets human NFIA.

21. The method of claim 20, wherein said shRNA comprises SEQ ID NO: 1.

22. The method of claim 18, wherein the NFIA inhibitor comprises a viral expression vector that comprises said NFIA antisense polynucleotide.

23. The method of claim 9, wherein said NFIA inhibitor is an antibody that specifically binds to NFIA.

24. An antisense polynucleotide comprising an isolated polynucleotide comprising a nucleic acid that is at least 90% identical to SEQ ID NO: 1.

* * * * *